US007342038B2

(12) United States Patent
Brugnara et al.

(10) Patent No.: US 7,342,038 B2
(45) Date of Patent: Mar. 11, 2008

(54) SUBSTITUTED DIPHENYL INDANONE, INDANE AND INDOLE COMPOUNDS AND ANALOGUES THEREOF USEFUL FOR THE TREATMENT OR PREVENTION OF DISEASES CHARACTERIZED BY ABNORMAL CELL PROLIFERATION

(75) Inventors: Carlo Brugnara, Newton Highlands, MA (US); Jose Halperin, Brookline, MA (US); Rudolf Fluckiger, Brookline, MA (US); Emile M. Bellott, Jr., Beverly, MA (US); Richard John Lombardy, Littleton, MA (US); John J. Clifford, Bedford, MA (US); Ying-Duo Gao, Meshanie Station, NJ (US); Reem M. Haidar, Woburn, MA (US); Eugene W. Kelleher, Somerville, MA (US); Adel M. Moussa, Burlington, MA (US); Yesh P. Sachdeva, Concord, MA (US); Minghua Sun, Cambridge, MA (US); Heather N. Taft, Littleton, MA (US)

(73) Assignees: President and Fellow of Harvard College, Cambridge, MA (US); Children's Medical Center Corporation, Boston, MA (US); NuChem Pharmaceuticals Inc., Toronto (CA)

( * ) Notice: Subject to any disclaimer, the term of this patent is extended or adjusted under 35 U.S.C. 154(b) by 0 days.

(21) Appl. No.: 10/858,975

(22) Filed: Jun. 1, 2004

(65) Prior Publication Data
US 2004/0242563 A1 Dec. 2, 2004

Related U.S. Application Data

(62) Division of application No. 10/043,640, filed on Jan. 10, 2002, now Pat. No. 6,800,658.

(51) Int. Cl.
C07D 209/10 (2006.01)
C07D 209/12 (2006.01)
A61K 31/404 (2006.01)

(52) U.S. Cl. ............. 514/415; 548/469; 548/483; 548/490

(58) Field of Classification Search .......... 548/469, 548/483, 490; 514/415
See application file for complete search history.

(56) References Cited

U.S. PATENT DOCUMENTS

| 3,546,165 | A | 12/1970 | Morgan ................. 260/47 |
| 4,006,023 | A | 2/1977 | McLaughlin et al. ........ 96/90 |
| 4,806,685 | A | 2/1989 | Abraham et al. .......... 564/324 |
| 4,988,785 | A | 1/1991 | Paul et al. ............... 526/259 |
| 5,273,992 | A | 12/1993 | Brugnara et al. .......... 514/398 |
| 5,358,959 | A | 10/1994 | Halperin et al. .......... 514/396 |
| 5,430,062 | A | 7/1995 | Cushman et al. .......... 514/646 |
| 5,512,563 | A | 4/1996 | Albright et al. .......... 514/217 |
| 6,800,658 | B2* | 10/2004 | Brugnara et al. .......... 514/467 |
| 2002/0128256 | A1 | 9/2002 | Brugnara et al. ....... 514/212.02 |

FOREIGN PATENT DOCUMENTS

| DE | 3706427 | | 9/1988 |
| DE | 10004654 | | 8/2001 |
| EP | 0 323 740 A2 | | 7/1989 |
| EP | 483632 | | 5/1992 |
| EP | 0 583 665 A2 | | 2/1994 |
| EP | 0 636 608 A1 | | 2/1995 |
| JP | 05 050771 | | 3/1993 |
| JP | 05 58894 | | 3/1993 |
| WO | WO 89/02741 | * | 4/1989 |
| WO | WO 89/08096 | | 9/1989 |
| WO | WO 95/26720 | | 10/1995 |
| WO | WO 96/08240 | | 3/1996 |
| WO | WO 96/08242 | | 3/1996 |
| WO | WO 96/36631 | | 11/1996 |
| WO | WO 99/26624 | | 6/1999 |
| WO | WO 02/32465 | | 4/2002 |

OTHER PUBLICATIONS

Matevosyan et al., CAPLUS Abstract 55:18704f-i, 1961.*
Samoilova et al., CAPLUS Abstract 93:7272, 1980.*
Varga et al., CAPLUS Abstract 117:277 (1992).*
Kawada et al., CAPLUS Abstract 124:216109, 1996.*
*Aldrich Catalog*, 1994-1995: Compounds 13, 484-8; T8,380-1; 10,130-3; D21,320-9; 32,543-0; 35,890-8; T8,160-4; 25,657-9; T8,470-0; T8,417-7; T8,360-7; S36,533-5; S50,949-3; 37,411-3; 37,152-1; 30,151-5; 27,520-4; 34,182-7; 35,889-4; S84,240-0; S79,226-8; 27,519-0; S64,640; S81,477-6; 36,005-8; S70,627-2; S34,966-6; S87,739-5; 11,500-2; S83,881-0; S58,110-0; 21,560-0; S91,408-8; S60,147-0; S83,571-4; S82,654-5; S8,388-2; S94,371-1; S87,649-6; S83,719-9; S83,042-9; S82,162-4; S81,468-7; S82,290-6; S79,387.

(Continued)

*Primary Examiner*—Deepak Rao
(74) *Attorney, Agent, or Firm*—Mastermind IP Law P.C.; Diane L. Gardner

(57) ABSTRACT

The present invention provides substituted 3,3-diphenyl indole compounds, as well as analogues thereof, which are specific potent and safe inhibitors of mammalian cell proliferation. The compounds can be used to inhibit mammalian cell proliferation in situ as a therapeutic approach towards the treatment or prevention of diseases characterized by abnormal cell proliferation, such as cancer.

15 Claims, 2 Drawing Sheets

OTHER PUBLICATIONS

Figure 1:
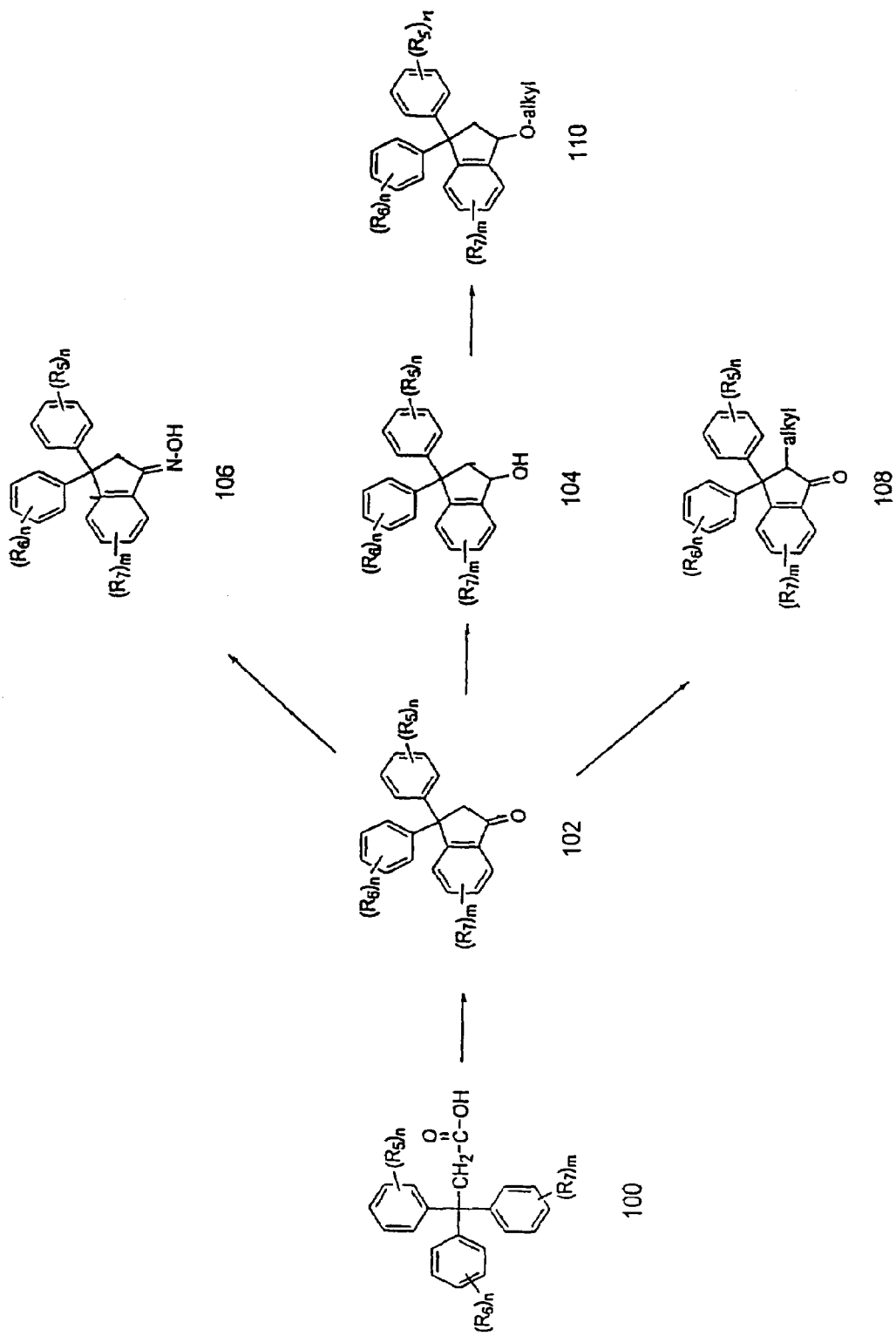

Ando, W., et al., "A Novel Reduction of α-Aryl Alkanols by Diiododimethylsilane," *Tetrahedron Letters*, 51:4941-4942 (1979).
Barili et al., Chem. Abstract, 107:58774, 1987.
Barton, D. H. R., et al., "Pentavalent Organobismuth Reagents. Part 3. Phenylation of Enols and of Enolate and Other Anions," *J. Chem. Soc. Perkin Trans.*, 1:2667-2675 (1985).
Barton, D. H. R., et al., "Pentavalent Organobismuth Reagents. Part 3. Phenylation of Enols and of Enolate and Other Anions," *General Org. Chem.*, 105:531, col. 2, Abstract No. 208158b (1986).
Bartroli, J., et al., "Synthesis and Antifungal Activity of a Series of Difluorotritylimidazoles," *Arzneim.-Forsch./Drug Res.*, 42[I](6):832-835 (1992).
Benjamin, L. J., et al., "A Collaborative, Double-Blind Randomized Study of Cetiedil Citrate in Sickle Cell Crisis," *Blood*, 67(5):1442-1447 (1986).
Benzaquen, L. R., et al., "Clotrimazole Inhibits Cell Proliferation in vitro and in vivo," *Nature Medicine*, 1(6):534-540 (1995).
Bergman, J., et al., "Synthesis and Studies of Tris-Indolobenzenes and Related Compounds," *Tetrahedron*, 36:1445-1450 (1980).
Bergman, J., et al., "Synthesis and Studies of Tris-Indolobenzenes and Related Compounds," *Chemical Abstracts*, 94:368, col. 1, Abstract No. 3948s (1981).
Berkowitz, L. R., et al., "An Analysis of the Mechanism by Which Cetiedil Inhibits the Gardos Phenomenon," *American Journal of Hematology*, 17:217-223 (1984).
Beutler, E., et al., "The Removal of Leukocytes and Platelets from Whole Blood," *J. Lab. Clin Med.*, 88(2):328-333 (1976).
Bontems, F., et al., "Analysis of Side-Chain Organization on a Refined Model of Charybdotoxin: Structural and Functional Implications," *Biochemistry*, 31:7756-7764 (1992).
Brugnara, C., et al., "Oral Administration of Clotrimazole and Blockade of Human Erythrocyte Ca++-Activated K+ Channel: The Imidazole Ring is Not Required for Inhibitory Activity," *J. Pharmacology and Experimental Therapeutics*, vol. 273, No. 1, pp. 266□272 (1995).
Brugnara, C., et al., "$Ca^{2+}$-Activated $K^+$ Transport in Erythrocytes," *Journal of Biological Chemistry*, 268(12):8760-8768 (1993).
Brugnara, C., et al., "Inhibition of $Ca^{2+}$-Dependent $K^+$ Transport and Cell Dehydration in Sickle Erythrocytes by Clotrimazole and Other Imadazole Derivatives," *J. Clin. Invest.*, 92:520-526 (1993).
Brugnara, C., et al., "Inhibition of Gardos Channel and Red Cell Dehydration by Oral Administration of Clotrimazole in Sickle Cell Disease," *Blood*, 220a:865 (1994).
Brugnara, C., et al., "Inhibition of Gardos Channel and Red Cell Dehydration by Oral Administration of Clotrimazole in Sickle Cell Disease," *The 20th Annual Meeting of the National Sickle Cell Program*, p. 138 (1995).
Brugnara, C., et al., "Erythrocyte Gardos Channel and Sickle Cell Disease: Pathophysiology and Clinical Significance," *Advanced Course and International Symposium on "Membrane Transporters and Channels" Program and Abstracts*, Lecture 34 (1995).
Brugnara, C., et al., "Therapy with Oral Clotrimazole Induces Inhibition of the Gardos Channel and Reduction of Erythrocyte Dehydration in Patients with Sickle Cell Disease," *J. Clin. Invest.*, 97(5):1227-1234 (1996).
Burgess, M.A., et al., "Clotrimazole (Bay b 5097): In Vitro and Clinical Pharmacological Studies," *Antimicrobial Agents and Chemotherapy*, 2(6):423-426 (1972).
Byers, H.R., et al., "Organ-Specific Metastases in Immunodeficient Mice Injected with Human Melanoma Cells: a Quantative Pathological Analysis," *Melanoma Research*, 3:247-253 (1993).
Carter, A. J., et al., "Morphologic Characteristics of Lesion Formation and Time Course of Smooth Muscle Cell Proliferation in a Porcine Proliferative Restenosis Model," *JACC*, 24(5):1398-1405 (1994).
Charache, S., et al., "Failure of Desmopressin to Lower Serum Sodium or Prevent Crisis in Patients with Sickle Cell Anemia," *Blood*, 58(5):892-896 (1981).
Charache, S., et al., "Effect of Hydroxyurea on the Frequency of Painful Crises in Sickle Cell Anemia," *The New England Journal of Medicine*, 332(20):1317-1322 (1995).

Clark, M. R., et al., "Hydration of Sickle Cells Using the Sodium Ionophore Monensin," *J. Clin. Invest.*, 70:1074-1080 (1982).
Chun, Moon Woo et al. "Reactivity of 3-Haloindolenines", Chemical Abstracts, vol. 96, No. 17, Apr. 26, 1982, pp. 735.
Conte, L., et al., "Percutaneous Absorption and Skin Distribution of [$^{14}$C]Flutrimazole in Mini-pigs," *Arzneim.-Forsch./Drug Res.*, 42[I](6):847-853 (1992).
Conte, L., et al., "Pharmacokinetic Study of [$^{14}$C]Flutrimazole after Oral and Intravenous Administration in Dogs," *Arzneim.-Forsch./Drug Res.*, 42[I](6):854-858 (1992).
Corbett, T. H., "Preclinical Anticancer Activity of Cryptophycin-8," *Journal of Experimental Therapeutics & Oncology*, 1:95-108 (1996).
Dakkouri et al, Chem. Abstract 126:305266, 1997.
Dakkouri et al., "Effect of Dielectric Constant and Ionic Strength on the Fading of N, N-Dimethylaminophenolphthalein in Alkaline Medium", Chemical Abstract vol. 126, No. 23, Jun. 9, 1997, J. Chemical Education, 1997 74(5):556-559.
DeFranceschi, L., et al., "Treatment with Oral Clotrimazole Blocks $Ca^{2+}$-Activated $K^+$ Transport and Reverses Erythrocyte Dehydration in Transgenic SAD Mice," *J. Clin. Invest.*, 93:1670-1676 (1994).
Grossi-Paoletti, E., et al., "Lipids in Brain Tumors," *J. Neurosurg.*, 34:454-455 (1971).
Guy, R. B., et al., "In Vitro and In Vivo Effect of Hypotonic Saline on the Sickling Phenomenon," *American Journal of Medical Sciences*, 266(1):267-277 (1973).
Hanessian, S., et al., "Ethers and Anhydrosugars," *Methods Carbohydr. Chem.*, 7:63-67 (1976).
Hendrickson et al., Chem. Abstract No. 110:113878, 1989.
Hoch, J. M., et al., "Methods de synthese generale des acetonitriles trisubstitues de la formule generale," *Acadamie Des Sciences*, 245:73-75 (1957).
Holt, R. J., "Laboratory Assessment of the Antimycotic Drug Clotrimazole," *J. Clin. Path.*, 25:1089-1097 (1972).
Hoogerheide, J. G., et al., "Clotrimazole," *Analytical Profiles of Drug Substances*, 11:225-255 (1982).
Hsueh, A., "Designer Contraceptive Pills," Human Reproduction, vol. 10, No. 8, pp. 1997□2000 (1995).
Illes, Z., et al., "Application of Modified Silica Gels in the Pesticide Analysis II. Thin-Layer Chromatography of Benzonitrile and Triphenylmethane Derivatives," *Acta Phytopathologica et Entomologica Hungarica*, 23(1-2):243-255 (1988).
Isobe, M., et al., "Studies on 3H-Indole. I. General Synthetic Route of 3,3-Disubstituted 3H-Indoles via the Corresponding Oxindoles and then Indolines," *Yakugaku Zasshi*, 94(3):343-350 (1974).
Isobe, M., et al., "General Synthetic Route of 3,3-Disubstituted 3H-Indoles via the Corresponding Oxindoles and then Indolines," *Chemical Abstracts*, 81:448, col. 1, Abstract No. 77766j (1974).
Izquierdo, I., et al., "Local and Systemic Tolerance of Flutrimazole Skin Creams Following Single and Repeated Topical Application in Healthy Volunteers," *Arzneim.-Forsch./Drug Res.*, 42[I](6):859-860 (1992).
K.M. Johnston et al., "Friedel-Crafts Cyclisation-IV Intramolecular vs Intermolecular Acylation with J-Aryl Derivatives of Propionyl Chloride in Aromatic Substrates", Tetrahedron, vol. 30, No. 22, 1974, pp. 4059-4064.
Koelsch, Chem. Abstract 55:9360, 1961.
L.L. Miller et al., "The Thermolysis of Substituted Indenes. Sigmatropic Phenyl and Hydrogen Migrations," J. of American Chemical Society, 93:3, Feb. 10, 1971, pp. 650-656.
Lewis, T. W., et al., "Solid State Dehydration of (o-Hydroxyaryl)diphenylmethanols. Crystal and Molecular Structures of [1-(2-Hydroxyphenyl)]diphenylmethanol and of [1-(2-Hydroxynaphthyl)]diphenylmethanol," *J. Am. Chem. Soc.*, 102:4659-4664 (1980).
Li, F., et al., "Antitumor Activity of 1-Triphenylgermyl-4-Propiono-Substituted Semicarbazides, Thiosemicarbazides and Their Heterocyclic Derivatives," *Metal Based Drugs*, 3(5):241-242 (1996).
Liu, M. T. H., et al., "Equilibrium Constants for Triphenylmethyl Bromide and 3-Bromo-3-phenyldiazirine in Acetonitrile," *Tetrahedron Letters*, 28(33):3763-3766 (1987).
Manning et al., Chem. Abstract, 94:102538, 1981.

Maurice, M., et al., "Effects of Imidazole Derivatives on Cytochromes P450 from Human Hepatocytes in Primary Culture," The FASEB Journal, vol. 6, pp. 752–758 (1992).

Matsuura, Y., et al., "Structure-Activity Relationships in the Induction of Hepatic Microsomal Cytochrome P450 by Clotrimazole and its Structurally Related Compounds in Rats," *Biochemical Pharmacology*, 41(12):1949-1956 (1991).

Miller et al., Chem. Abstract No. 74:75859, 1971.

Miller, C., et al., "Charybdotoxin, a Protein Inhibitor of Single $Ca^{2+}$-activated $K^+$ Channels from Mammalian Skeletal Muscle," *Letters to Nature*, 313:316-318 (1985).

Montero, M., et al., "Agonist-Induced $Ca^{2+}$ Influx in Human Neutrophils is Secondary to the Emptying of Intracellular Calcium Stores," *Biochemical Journal*, 277:73-79 (1991).

Murphy, L., "Growth Factors and Steroid Hormone Action in Endometrial Cancer," J. Steroid Biochem. Molec. Biol., vol. 48, No. 5/6, pp. 419–423 (1994).

Najid, A., et al., Chem. Abstract 116: 187584x (1992).

Najid, A., et al., "Comparative Studies of Steroidogensis Inhibitors (Econazole, Ketoconazole) on Human Breast Cancer MCF-7 Cell Proliferation by Growth Experiments, Thymidine Incorporation and Flow Cytometric DNA Analysis," Tumori, vol. 77, pp. 385–390 (1991).

Nardone, P., et al., "Ketocanzole: A Thromboxane Synthetase and 5-Lipoxygenase Inhibitor with Antimetastatic Activity in B16-F10 Melanoma," J. Surg. Res., vol. 44, pp. 425–429 (1988).

Nishio, T., et al., "A Novel Route to Indolines by Photochemical Desulphurization of Indoline-2-thiones," *J. Chem. Soc., Chem. Commun.*, 9:572-573 (1988).

Nishio, T., et al., "A Novel Route to Indolines by Photochemical Desulphurization of Indoline-2-thiones," *Chemical Abstracts*, 109:696, col. 2, Abstract No. 170175x (1988).

O'Donnell, M. J., et al., "Synthesis and Properties of a Hoechst-Like Minor-Groove Binding Agent Tethered to an Oligodeoxynucleotide," *Bioorganic & Medicinal Chemistry*, 3(6):743-750 (1995).

Olson, J., "Laboratory Evidence for the Hormonal Dependency of Meningiomas," Human Reproduction, vol. 9, Supp. 1, pp. 195–201 (1994).

Omenn, Cancer Prevention, Cecil Textbook of Medicine, 20th Edition, vol. 2, pp. 1008-1010, 1996.

Owens, N. J., et al., "Prophylaxis of Oral Candidiasis with Clotrimazole Troches," *Arch. Intern. Med.*, 144:290-293 (1984).

Paike, N. H., "Dissociation Constants for Triphenylmethyl Halides and 3-phenyl-3-halodiazirines," Materials Science, 18(1):53-57 (1992).

Paoletti, P., et al., "Drugs Acting on Brain Tumor Sterols," *The Experimental Biology of Brain Tumors*, pp. 457-479 (1972).

Pappas, J. B., et al., "Hepatic Clotrimazole Concentrations and Hepatic Drug Metabolizing Enzyme Activities in Adult Mail Sprague-Dawley Rats," *Toxicology*, 80:27-35 (1993).

Park, C., et al., "Design, Synthesis, and Functional Expression of a Gene for Charybdotoxin, a Peptide Blocker of $K^+$ Channels," *Proc. Natl. Acad. Sci. USA*, 88:2046-2050 (1991).

Peppelenbosch, M. P., et al., "Epidermal Growth Factor-activated Calcium and Potassium Channels," *Journal of Biological Chemistry*, 266(3):19938-19944 (1991).

Perrine, S. P., et al., "A Short-Term Trial of Butyrate to Stimulate Fetal-Globin-Gene Expression in the β-Globin Disorders," *The New England Journal of Medicine*, 328(2):81-86 (1993).

Petersen, P. M., "Synthesis of Heterocycles Containing Two Cytosine or Two Guanine Base-Pairing Sites. Novel Tectons for Self-Assembly," *Bioorganic & Medicinal Chemistry*, 4(7):1107-1112 (1996).

Trudel, M., et al., "Towards a Transgenic Mouse Model of Sickle Cell Disease: Hemoglobin SAD," *The EMBO Journal*, 10(11):3157-3165 (1991).

Vasquez, J., et al., "Characterization of High Affinity Binding Sites for Charybdotoxin in Sarcolemmal Membranes from Bovine Aortic Smooth Muscle," *The Journal of Biological Chemistry*, 264(35):20902-20909 (1989).

Vericat, M. L., et al., "Toxicity Studies with Flutrimazole," *Arzneim.-Forsch./Drug Res.*, 42[I](6):841-846 (1992).

Villalobos, C., et al., "Inhibition of Voltage-Gated $Ca^{2+}$ Entry into $GH_3$ and Chromaffin Cells by Imidazole Antimycotics and Other Cytochrome P450 Blockers," *FASEB Journal*, 6(8):2742-2747 (1992).

Westley, B., et al., "Role of Insulin-like Growth Factors in Steroid Modulated Proliferation," J. Steroid Biochem. Molec. Biol., vol. 51, No. 1/2, pp. 1–9 (1994).

Weuta, H., "Clinical Studies with Oral Clotrimazole," *Postgraduate Medical Journal*, Jul. Supp., pp. 45-48 (1974).

Wyche, J. H., et al., "Growth Regulation of Cultured Human Pituitary Cells by Steroidal and Nonsteroidal Compounds in Defined Medium," *Endocrinology*, 104(6):1765-1773 (1979).

Zhu, B., et al., "Effects of Etidronate and Lovastatin on the Regression of Artherosclerosis in Cholesterol-Fed Rabbits," *Cardiology*, 85:370-377 (1994).

DeFranceschi, L., et al., "Reduction of K-Cl Cotransport-Mediated Erythrocyte Dehydration by Dietary Magnesium Supplements in Patients with Sickle Cell Disease," *Blood*, 548a:2580 (1996).

DiMattina, M., et al., "Ketoconazole Inhibits Multiple Steroidogenic Enzymes Involved in Androgen Biosynthesis in the Human Ovary," Fertility and Sterility, vol. 49, No. 1, pp. 62–65 (1988).

Duchene, P., et al., "Pharmacokinetic Profile of [$^{14}$C]Flutrimazole Following Single Topical Application in Normal and Scarified Skin of Healthy Volunteers," *Arzneim.-Forsch./Drug Res.*, 42[I](6):861-863 (1992).

Duhm, B., et al., "The Pharmacokinetics of Clotrimazole $^{14}$C," *Postgraduate Medical Journal*. Jul. Supp.:13-16 (1974).

Dykes, D. J., et al., "Development of Human Tumor Xenograft Models for In Vivo Evaluation of New Antihumor Drugs," *Immunodeficient Mice in Oncology*, 42:1-22 (1992).

Engelhardt, et al., "Therapy of Cushing's Syndrome with Steroid Biosynthesis Inhibitors," J. Steroid Biochem. Molec. Biol., vol. 49, No. 4-6, pp. 261–267 (1994.

Enokida et al., Chem. Abstract 126:39836, 1996.

Epstein, R. J., et al., "Corneal Neovascularization," *Cornea*, 6(4):250-257 (1987).

Ethridge, D. E., et al., "Economic Weed Control in High Plains Cotton," *J. Prod. Agric.*, 3(2):246-252 (1990).

Fahim, M., et al., "Cardiovascular Effects and Pharmacokinetics of the Carboxylic Ionophore Monensin in Dogs and Rabbits," *Life Sciences*, 29:1959-1966 (1981).

Fan, et al., Yiyao Gongye, 9:2-4 (1983).

Ferguson, G., et al., "The Structure of Triphenylgermanium Hydroxide," *Acta Cryst.*, 48:1228-1231 (1992).

Fingl, E., et al., "General Principals," *The Pharmacological Basis of Therapeutics*, 1:1-46 (1975).

Fleming, I., et al., "Two New Stereochemically Complementary Oxindole Syntheses," *Tetrahedron Letters*, 23(19):2053-2056 (1982).

Ian Fleming et al., "Two New Oxindole Syntheses", J. Chemical Society, 1986, pp. 349-359.

Forgue-Lafitte, M., et al., "Effects of Ketoconazole on the Proliferation and Cell Cycle of Human Cancer Cell Lines," Cancer Res., vol. 52, pp. 6827–6831 (1992).

Gagnon, Beilstein No. 4924895, 1929.

Gait, M. J., "An Introduction to Modern Methods of DNA Synthesis," *Introduction to DNA Synthesis*, 1:1-22, 1984.

Gait, M. J., "Oligonucleotide Synthesis, A Practical Approach," *IRL Press*, Oxford, pp. 13 and 76 (1984).

Glidewell, C., et al., "Molecules Isoelectronic with 2, 2, 2-Triphenylethanol: Multiple Hydrogen-Bonding Modes in the Structures of O-Trithythydroxylamine, $Ph_3CONH_2$, and Triphenylmethanesulfenamide, $Ph_3CSNH_2$," *Acta Cryst.*, 50: 1362-1366 (1994).

Goldberg, M. A., et al., "Treatment of Sickle Cell Anemia with Hydroxyurea and Erythropoietin," *New England Journal of Medicine*, 323(6):366-372 (1990).

Grinstein, S., et al., "Calcium-Independent Cell Volume Regulation in Human Lymphocytes," *The Journal of General Physiology*, 95:97-120 (1990).

Ponnuswamy, M. N., et al., "Acetyltriphenylmethane, *$C_{21}H_{18}O$," *Acta Cryst.*, 40:142-144 (1984).

Rafanell, J. G., et al., "In vitro and in vivo Studies with Flutrimazole, a New Imidazole Derivative with Antifungal Activity," *Arzneim.-Forsch./Drug Res.*, 42[I](6):836-840 (1992).

Rideout, D.C., et al., "Phosphonium Salts Exhibiting Selective Anti-Carcinoma Activity in vitro," *Anti-Cancer Drug Design*, 4:265-280 (1989).

R.F. Brown et al., "Hydrogen Transfer. Part XVI The Synthesis and Cyclodehydrogenation of 2-Diphenylmethylstyrene", J. Chemical Society, 1960, pp. 3144-3147.

Rideout, D., et al., "Mechanism of Inhibition of FaDu Hypopharyngeal Carcinoma Cell Growth by Tetraphenylphosphonium Chloride," *Int. J. Cancer*, 57:247-253 (1994).

Ritter, W., et al., "Pharmacokinetic Fundamentals of Vaginal Treatment with Clotrimazole," *Chemotherapy*, 28 (Supp. 1):37-42 (1982).

Rifai, N., et al., "HPLC Measurement, Blood Distribution, and Pharmacokinetics or Oral Clotrimazole, Potentially Useful Antisickling Agent," Clin. Chem., vol. 41, No. 3, pp. 387–391 (1995).

Ritter, W., "Pharmacokinetic Fundamentals of Vaginal Treatment with Clotrimazole," *Am. J. Obster. Gynecol.*, 152(7 part 2):945-947 (1985).

Rosa, R. M., et al., "A Study of Induced Hyponatremia in the Prevention and Treatment of Sickle-Cell Crisis," *The New England Journal of Medicine*, 303(20):1138-1143 (1980).

Rosnati et al., Chem. Abstract 110:153506, 1989.

Rubright, W. C., et al., "Ultrastructural Changes Produced by Triparanol in Morris 5123 and Novikoff Hepatomas," *Cancer Research*, 27:165-171 (1967).

Sakuta, M., et al., "Potent Antitumor Agents with Low Toxicity," *Chemical Abstracts*, 119:92, col. 2, Abstract No. 63033j (1993).

Sasakura et al., Synthesis of 11-pheny-5, 6-dihydro-11H-dibenz(b,e)azepine derivatives, Heterocycles, vol. 15, No. 1, pp. 421-425, 1981.

Sawyer, P. R., et al., "Clotrimazole: A Review of its Antifungal Activity and Therapeutic Efficacy," *Drugs*, 9:424-447 (1975).

Simon, Oncology: Introduction, Cecil Textbook of Medicine, 20th Edition, vol. 1, pp. 1004-1008, 1996.

Simig, G., et al., "On the Mechanism of Formation of Dimeric and Reduced Products from an $\alpha$-Halo Amide with Sodium Methoxide," *Tetrahedron*, 34:2371-2374 (1978).

Starnes, Jr., Chem. Abstract 69:43555, 1968.

Stuart, J., et al., "Oxpentifylline and Cetiedil Citrate Improve Deformability of Dehydrated Sickle Cells," *Journal of Clinical Pathology*, 40(10):1182-1186 (1987).

Stuart, J., et al., "Additive in vitro Effects of Anti-Sickling Drugs," *British Journal of Hematology*, 86:820-823 (1994).

Tzanakakis, G., et al., "Inhibition of Hepatic Metastasis from a Human Pacreatic Adenocarcinoma (RWP-2) in the Nude Mouse by Prostacyclin, Forskolin, and Ketoconazole," Cancer, vol. 65, pp. 446–451 (1990).

Tomioka, K., et al., "Highly Stereoselective Construction of Chiral Quaternary Carbon: Asymmetric Synthesis of $\beta$, $\beta$-Disubstituted $\gamma$-Butyrolactones," *Chemistry Letters*, pp. 1621-1624 (1981).

* cited by examiner

US 7,342,038 B2

SUBSTITUTED DIPHENYL INDANONE, INDANE AND INDOLE COMPOUNDS AND ANALOGUES THEREOF USEFUL FOR THE TREATMENT OR PREVENTION OF DISEASES CHARACTERIZED BY ABNORMAL CELL PROLIFERATION

This application is a divisional (and claims the benefit of priority under 35 USC 120) of U.S. application Ser. No. 10/043,640, filed Jan. 10, 2002 now U.S. Pat. No. 6,800,658, which claims benefit of U.S. application Ser. No. 09/554,849, filed Sep. 22, 2000, now abandoned, which claims benefit of Ser. No. 09/535,077, filed Mar. 23, 2000, now abandoned, which claims benefit of Ser. No. 09/472,859, filed Dec. 27, 1999 which claims priority under 371 of PCT/US98/24819, filed Nov. 20, 1998, which claims benefit of Ser. No. 08/975,391, filed Nov. 20, 1997, now abandoned. The disclosure of the prior applications is considered part of (and is incorporated by reference in) the disclosure of this application.

1. FIELD OF THE INVENTION

The present invention relates to aromatic organic compounds which are specific, potent and safe inhibitors of the $Ca^{2+}$-activated potassium channel (Gardos channel) of erythrocytes and/or of mammalian cell proliferation. The compounds can be used to reduce sickle erythrocyte dehydration and/or delay the occurrence of erythrocyte sickling or deformation in situ as a therapeutic approach towards the treatment or prevention of sickle cell disease. The compounds can also be used to inhibit mammalian cell proliferation in situ as a therapeutic approach towards the treatment or prevention of diseases characterized by abnormal cell proliferation.

2. BACKGROUND OF THE INVENTION

Sickle cell disease has been recognized within West Africa for several centuries. Sickle cell anemia and the existence of sickle hemoglobin (Hb S) was the first genetic disease to be understood at the molecular level. It is recognized today as the morphological and clinical result of a glycine to valine substitution at the No. 6 position of the beta globin chain (Ingram, 1956, *Nature* 178:792-794. The origin of the amino acid change and of the disease state is the consequence of a single nucleotide substitution (Marotta et al., 1977, *J. Biol. Chem.* 252:5040-5053).

The major source of morbidity and mortality of patients suffering from sickle cell disease is vascular occlusion caused by the sickled cells, which causes repeated episodes of pain in both acute and chronic form and also causes ongoing organ damage with the passage of time. It has long been recognized and accepted that the deformation and distortion of sickle cell erythrocytes upon complete deoxygenation is caused by polymerization and intracellular gelation of sickle. hemoglobin, hemoglobin S (Hb S). The phenomenon is well reviewed and discussed by Eaton and Hofrichter, 1987, *Blood* 70:1245. The intracellular gelatin and polymerization of Hb S can occur at any time during erythrocyte's journey through the vasculature. Thus, erythrocytes in patients with sickle cell disease containing no polymerized hemoglobin S may pass through the microcirculation and return to the lungs without sickling, may sickle in the veins or may sickle in the capillaries.

The probability of each of these events is determined by the delay time for intracellular gelation relative to the appropriate capillary transit time (Eaton et al., 1976, *Blood* 47:621). In turn, the delay time is dependent upon the oxygenation state of the hemoglobin, with deoxygenation shortening the delay time. Thus, if it is thermodynamically impossible for intracellular gelation to take place, or if the delay time at venous oxygen pressures is longer than about 15 seconds, cell sickling will not occur. Alternatively, if the delay time is between about 1 and 15 seconds, the red cell will likely sickle in the veins. However, if the delay time is less than about 1 second, red cells will sickle within the capillaries.

For red cells that sickle within the capillaries, a number of possible consequent events exist, ranging from no effect on transit time, to transient occlusion of the capillary, to a more permanent blockage that may ultimately result in ischemia or infarction of the surrounding cells, and in destruction of the red cell.

It has long been recognized that the cytoplasm of the normal erythrocyte comprises approximately 70% water. Water crosses a normal erythrocyte membrane in milliseconds; however, the loss of cell water causes an exponential increase in cytoplasmic viscosity as the mean cell hemoglobin concentration (MCHC) rises above about 32 g/dl. Since cytoplasmic viscosity is a major determinate of erythrocyte deformability and sickling, the dehydration of the erythrocyte has substantial rheological and pathological consequences. Thus, the physiological mechanisms that maintain the water content of normal erythrocytes and the pathological conditions that cause loss of water from erythrocytes in the blood circulation are critically important. Not surprisingly, regulation of erythrocyte dehydration has been recognized as an important therapeutic approach towards the treatment of sickle cell disease. Since cell water will follow any osmotic change in the intracellular concentration of ions, the maintenance of the red cell's potassium concentration is of particular importance (Stuart and Ellory, 1988, *Brit J. Haematol.* 69:1-4).

Many attempts and approaches to therapeutically treating dehydrated sickle cells (and thus decreasing polymerization of hemoglobin S by lowering the osmolality of plasma) have been tried with limited success, including the following approaches: intravenous infusion of distilled water (Gye et al., 1973, *Am. J. Med. Sci.* 266:267-277); administration of the antidiuretic hormone vasopressin together with a high fluid intake and salt restriction (Rosa et al., 1980, *M. Eng. J. Med.* 303:1138-1143; Charache and Walker, 1981, *Blood* 58:892-896); the use of monensin to increase the cation content of the sickle cell (Clark et al., 1982, *J. Clin. Invest.* 70:1074-1080; Fahim and Pressman, 1981, *Life Sciences* 29:1959-1966); intravenous administration of cetiedil citrate (Benjamin et al., 1986, *Blood* 67:1442-1447; Berkowitz and Orringer, 1984, *Am. J. Hematol.* 17:217-223; Stuart et al., 1987, *J. Clin. Pathol.* 40:1182-1186); and the use of oxpentifylline (Stuart et al., 1987, *J. Clin. Pathol.* 40:1182-1186).

Another approach towards therapeutically treating dehydrated sickle cells involves the administration of imidazole, nitroimidazole and triazole antimycotic agents such as Clotrimazole (U.S. Pat. No. 5,273,992 to Brugnara et al.). Clotrimazole, an imidazole-containing antimycotic agent, has been shown to be a specific, potent inhibitor of the Gardos channel of normal and sickle erythrocytes, and prevents $Ca^{2+}$-dependent dehydration of sickle cells both in vitro and in vivo (Brugnara et al., 1993, *J. Clin. Invest.* 92:520-526; De Franceschi et al., 1994, *J. Clin. Invest.* 93:1670-1676). When combined with a compound which stabilizes the oxyconformation of Hb S, Clotrimazole induces an additive reduction in the clogging rate of a micropore filter and may attenuate the formation of irreversibly sickled cells (Stuart et al., 1994, *J. Haematol.* 86:820-823). Other compounds that contain a heteroaryl imidazole-like moiety believed to be useful in reducing sickle erythrocyte dehydration via Gardos channel inhibition include miconazole, econazole, butoconazole, oxiconazole and sulconazole. Each of these compounds is a known antimycotic. Other imidazole-containing compounds have been found to be incapable of inhibiting the Gardos channel and preventing loss of potassium.

As can be seen from the above discussion, reducing sickle erythrocyte dehydration via blockade of the Gardos channel is a powerful therapeutic approach towards the treatment and/or prevention of sickle cell disease. Compounds capable of inhibiting the Gardos channel as a means of reducing sickle cell dehydration are highly desirable, and are therefore an object of the present invention.

Cell proliferation is a normal part of mammalian existence, necessary for life itself. However, cell proliferation is not always desirable, and has recently been shown to be the root of many life-threatening diseases such as cancer, certain skin disorders, inflammatory diseases, fibrotic conditions and arteriosclerotic conditions.

Cell proliferation is critically dependent on the regulated movement of ions across various cellular compartments, and is associated with the synthesis of DNA. Binding of specific polypeptide growth factors to specific receptors in growth-arrested cells triggers an array of early ionic signals that are critical in the cascade of mitogenic events eventually leading to DNA synthesis (Rozengurt, 1986, *Science* 234:161-164). These include (1) a rapid increase in cystolic $Ca^{2+}$, mostly due to rapid release of $Ca^{2+}$ from intracellular stores; (2) capacitative $Ca^{2+}$ influx in response to opening of ligand-bound and hyperpolarization-sensitive $Ca^{2+}$ channels in the plasma membrane that contribute further to increased intracellular $Ca^{2+}$ concentration (Tsien and Tsien, 1990, *Annu. Rev. Cell Biol.* 6:715-760; Peppelenbosch et al., 1991, *J. Biol. Chem.* 266:19938-19944); and (3) activation of $Ca^{2+}$-dependent $K^+$ channels in the plasma membrane with increased $K^+$ conductance and membrane hyperpolarization (Magni et al., 1991, *J. Biol. Chem.* 261:9321-9327). These mitogen-induced early ionic changes, considered critical events in the signal transduction pathways, are powerful therapeutic targets for inhibition of cell proliferation in normal and malignant cells.

One therapeutic approach towards the treatment of diseases characterized by unwanted or abnormal cell proliferation via alteration of the ionic fluxes associated with early mitogenic signals involves the administration of clotrimazole. As discussed above, Clotrimazole has been shown to inhibit the $Ca^{2+}$-activated potassium channel of erythrocytes. In addition, Clotrimazole inhibits voltage- and ligand-stimulated $Ca^{2+}$ influx mechanisms in nucleated cells (Villalobos et al., 1992, *FASEB J.* 6:2742-2747; Montero et al., 1991, *Biochem. J.* 277:73-79) and inhibits cell proliferation both in vitro and in vivo (Benzaquen et al., 1995, *Nature Medicine* 1:534-540). Recently, Clotrimazole and other imidazole-containing antimycotic agents capable of inhibiting $Ca^{2+}$-activated potassium channels have been shown to be useful in the treatment of arteriosclerosis (U.S. Pat. No. 5,358,959 to Halperin et al.), as well as other disorders characterized by unwanted or abnormal cell proliferation.

As can be seen from the above discussion, inhibiting mammalian cell proliferation via alteration of ionic fluxes associated with early mitogenic signals is a powerful therapeutic approach towards the treatment and/or prevention of diseases characterized by unwanted or abnormal cell proliferation. Compounds capable of inhibiting mammalian cell proliferation are highly desirable, and are therefore also an object of the present invention.

3. SUMMARY OF THE INVENTION

These and other objects are provided by the present invention, which in one aspect provides a class of organic compounds which are potent, selective and safe inhibitors of the $Ca^{2+}$-activated potassium channel (Gardos channel) of erythrocytes, particularly sickle erythrocytes, and/or of mammalian cell proliferation. The compounds are generally substituted 3,3-diphenyl indanone, indane or (3-H) indole compounds, or analogues thereof. In one illustrative embodiment, the compounds capable of inhibiting the Gardos channel and/or mammalian cell proliferation according to the invention are compounds having the structural formula:

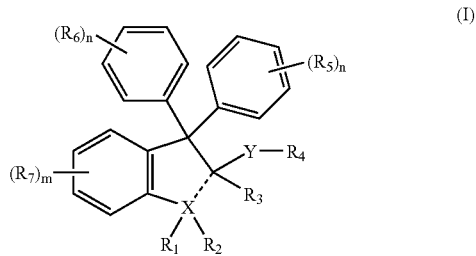

(I)

or pharmaceutically acceptable salts or hydrates thereof, wherein:

m is 0, 1, 2, 3 or 4;

each n is independently 0, 1, 2, 3, 4 or 5;

X is C or N;

Y is absent, ($C_1$-$C_6$) alkyl, ($C_1$-$C_6$) alkenyl or ($C_1$-$C_6$) alkynyl;

$R_1$ is absent, —OR, —SR, =O, =S, =N—OR, —O—C(O)R, —S—C(O)R, —O—C(S)R, —S—C(S)R, or when taken together with $R_2$ is a 3-8 membered heterocycloalkyl or a substituted 3-8 membered heterocycloalkyl;

$R_2$ is absent or —H;

$R_3$ is absent or —H;

$R_4$ is —H, —OR', —SR', —NR'$_2$, —CN, —NO$_2$, ($C_3$-$C_8$) cycloalkyl, 3-8 membered heterocycloalkyl, —C(O)R', —C(S)R', —C(O)OR', —C(S)OR', —C(O)SR', —C(S)SR', —C(O)NR'$_2$ or —C(S)NR'$_2$;

each $R_5$, $R_6$, and $R_7$ is independently selected from the group consisting of -halogen, —R', —OR', —SR', —NR'$_2$, —ONR'$_2$, —SNR'$_2$, —NO$_2$, —CN, —C(O)R', —C(S)R', —C(O)OR', —C(O)SR', —C(S)OR', —CS(S)R', —C(O)NR'$_2$, —C(S)NR'$_2$, —C(O)NR'(OR'), —C(S)NR'(OR'); —C(O)NR'(SR'), —C(S)NR'(SR'), —CH(CN)$_2$, —CH[C(O)R']$_2$, —CH[C(S)R']$_2$, —CH[C(O)OR']$_2$, —CH[C(S)OR']$_2$, —CH[C(O)SR']$_2$ and —CH[C(S)SR']$_2$;

each R is independently selected from the group consisting of —H, ($C_1$-$C_6$) alkyl, ($C_1$-$C_6$) alkenyl, ($C_1$-$C_6$) alkynyl, ($C_5$-$C_{20}$) aryl, substituted ($C_5$-$C_{20}$) aryl, ($C_6$-$C_{26}$) alkaryl and substituted ($C_6$-$C_{26}$) alkaryl;

the heterocycloalkyl substituents are each independently selected from the group consisting of —CN, —NO$_2$, —NR'$_2$, —OR', —C(O)NR'$_2$, —C(S)NR'$_2$, —C(O)OR', —C(S)OR', —C(O)SR', —C(S)SR' and trihalomethyl;

the aryl and alkaryl substituents are each independently selected from the group consisting of halogen, —C(O)R', —C(S)R', —C(O)OR', —C(S)OR', —C(O)SR', —C(S)SR', —C(O)NR'$_2$, —C(S)NR'$_2$ and trihalomethyl;

each R' is independently selected from the group consisting of —H, (C$_1$-C$_6$) alkyl, (C$_1$-C$_6$) alkenyl and (C$_1$-C$_6$) alkynyl; and

- - - designates a single or double bond.

In another aspect, the present invention provides pharmaceutical compositions comprising one or more compounds according to the invention in admixture with a pharmaceutically acceptable carrier, excipient or diluent. Such a preparation can be administered in the methods of the invention.

In still another aspect, the invention provides a method for reducing sickle erythrocyte dehydration and/or delaying the occurrence of erythrocyte sickling or deformation in situ. The method involves contacting a sickle erythrocyte in situ with an amount of at least one compound according to the invention, or a pharmaceutical composition thereof, effective to reduce sickle erythrocyte dehydration and/or delay the occurrence of erythrocyte sickling or deformation. In a preferred embodiment, the sickle cell dehydration is reduced and erythrocyte deformation is delayed in a sickle erythrocyte that is within the microcirculation vasculature of a subject, thereby preventing or reducing the vaso-occlusion and consequent adverse effects that are commonly caused by sickled cells.

In still another aspect, the invention provides a method for the treatment and/or prevention of sickle cell disease in a subject, such as a human. The method involves administering a prophylactically or therapeutically effective amount of at least one compound according to the invention, or a pharmaceutical composition thereof, to a patient suffering from sickle cell disease. The patient may be suffering from either acute sickle crisis or chronic sickle cell episodes.

In yet another aspect, the invention provides a method for inhibiting mammalian cell proliferation in situ. The method involves contacting a mammalian cell in situ with an amount of at least one compound according to the invention, or a pharmaceutical composition thereof, effective to inhibit cell proliferation. The compound or composition may act either cytostatically, cytotoxically or a by a combination of both mechanisms to inhibit proliferation. Mammalian cells in this manner include vascular smooth muscle cells, fibroblasts, endothelial cells, various types of pre-cancer cells and various types of cancer cells.

In still another aspect, the invention provides a method for treating and/or preventing unwanted or abnormal cell proliferation in a subject, such as a human. In the method, at least one compound according to the invention, or a pharmaceutical composition thereof, is administered to a subject in need of such treatment in an amount effective to inhibit the unwanted or abnormal mammalian cell proliferation. The compound and/or composition may be applied locally to the proliferating cells, or may be administered to the subject systemically. Preferably, the compound and/or composition is administered to a subject that has a disorder characterized by unwanted or abnormal cell proliferation. Such disorders include, but are not limited to, cancer, epithelial precancerous lesions, non-cancerous angiogenic conditions or arteriosclerosis.

In a final aspect, the invention provides a method for the treatment and/or prevention of diseases that are characterized by unwanted and/or abnormal mammalian cell proliferation. The method involves administering a prophylactically or therapeutically effective amount of at least one compound according to the invention, or a pharmaceutical composition thereof, to a subject in need of such treatment. Diseases that are characterized by abnormal mammalian cell proliferation which can be treated or prevented by way of the methods of the invention include, but are not limited to, cancer, blood vessel proliferative disorders, fibrotic disorders and arteriosclerotic conditions.

3.1 Definitions

As used herein, the following terms shall have the following meanings:

"Alkyl:" refers to a saturated branched, straight chain or cyclic hydrocarbon radical. Typical alkyl groups include, but are not limited to, methyl, ethyl, propyl, isopropyl, butyl, isobutyl, t-butyl, pentyl, isopentyl, hexyl, and the like. In preferred embodiments, the alkyl groups are (C$_1$-C$_6$) alkyl, with (C$_1$-C$_3$) being particularly preferred.

"Substituted Alkyl:" refers to an alkyl radical wherein one or more hydrogen atoms are each independently replaced with other substituents.

"Heterocycloalkyl:" refers to a saturated cyclic hydrocarbon radical wherein one or more of the carbon atoms are replaced with another atom such as Si, Ge, N, O, S or P. Typical heterocycloalkyl groups include, but are not limited to, morpholino, thiolino, piperadyl, pynolidinyl, piperazyl, pyrazolidyl and the like. Preferably, the heterocycloalkyl group contains 3-8 atoms. In a particularly preferred embodiment the heteroatoms are oxygen, and the heterocycloalkyl group is a 3-8 membered oxirane, preferably 2,3-oxirane or a 5-8 membered dioxycycloalkyl, preferably 1,3-dioxolanyl.

"Substituted Heterocycloalkyl:" refers to a heterocycloalkyl group wherein one or more hydrogen atoms are each independently replaced with other substituents.

"Alkenyl:" refers to an unsaturated branched, straight chain or cyclic hydrocarbon radical having at least one carbon-carbon double bond. The radical may be in either the cis or trans conformation about the double bond(s). Typical alkenyl groups include, but are not limited to, ethenyl, propenyl, isopropenyl, butenyl, isobutenyl, tert-butenyl, pentenyl, hexenyl and the like. In preferred embodiments, the alkenyl group is (C$_1$-C$_6$) alkenyl, with (C$_1$-C$_3$) being particularly preferred.

"Substituted Alkenyl:" refers to an alkenyl radical wherein one or more hydrogen atoms are each independently replaced with other substituents.

"Alkynyl:" refers to an unsaturated branched, straight chain or cyclic hydrocarbon radical having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is (C$_1$-C$_6$) alkynyl, with (C$_1$-C$_3$) being particularly preferred.

"Substituted Alkynyl:" refers to an alkynyl radical wherein one or more hydrogen atoms are each independently replaced with other substituents.

"Alkoxy:" refers to an —OR radical, where R is alkyl, alkenyl or alkynyl, as defined above.

"Alksulfanyl:" refers to an —SR radical, where R is alkyl, alkenyl or alkynyl, as defined above.

"Aryl:" refers to an unsaturated cyclic hydrocarbon radical having a conjugated π electron system. Typical aryl groups include, but are not limited to, penta-2,4-diene, phenyl, naphthyl, anthracyl, azulenyl, indacenyl, and the like. In preferred embodiments, the aryl group is (C$_5$-C$_{20}$) aryl, with (C$_5$-C$_{10}$) being particularly preferred.

"Substituted Aryl:" refers to an aryl radical wherein one or more hydrogen atoms are each independently replaced with other substituents.

"Alkaryl:" refers to a straight-chain alkyl, alkenyl or alkynyl group wherein one of the hydrogen atoms bonded to a terminal carbon is replaced with an aryl moiety. Typical alkaryl groups include, but are not limited to, benzyl, benzylidene, benzylidyne, benzenobenzyl, naphthenobenzyl and the like. In preferred embodiments, the alkaryl group is ($C_6$-$C_{26}$) alkaryl, i.e., the alkyl, alkenyl or alkynyl moiety of the alkaryl group is ($C_1$-$C_6$) and the aryl moiety is ($C_5$-$C_{20}$). In particularly preferred embodiments, the alkaryl group is ($C_6$-$C_{13}$) alkaryl, i.e., the alkyl, alkenyl or alkynyl moiety of the alkaryl group is ($C_1$-$C_3$) and the aryl moiety is ($C_5$-$C_{10}$).

"Substituted Alkaryl:" refers to an alkaryl radical wherein one or more hydrogen atoms on the aryl moiety of the alkaryl group are each independently replaced with other substituents.

"In Situ:" refers to and includes the terms "in vivo, flex vivo, " and "in vitro" as these terms are commonly recognized and understood by persons ordinarily skilled in the art. Moreover, the phrase "in situ" is employed herein in broadest connotative and denotative contexts to identify an entity, cell or tissue as found or in place, without regard to its source or origin, its condition or status or its duration or longevity at that location or position.

4. BRIEF DESCRIPTION OF THE DRAWINGS

Figure 2:
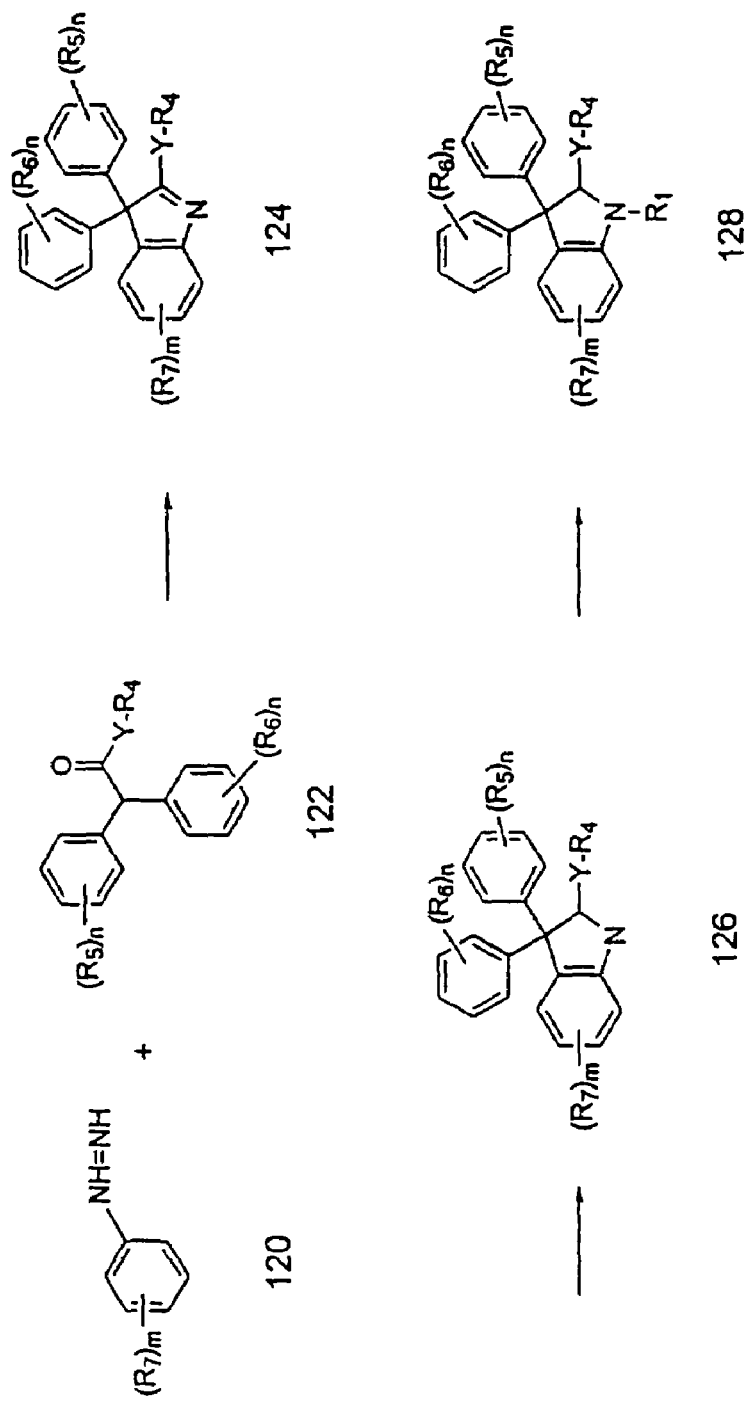

FIG. 1 is a general reaction scheme for synthesizing certain compounds according to the invention; and FIG. 2 is a general reaction scheme for synthesizing certain compounds according to the invention.

5. DETAILED DESCRIPTION OF THE INVENTION

As discussed in the Background section, blockade of sickle dehydration via inhibition of the Gardos channel is a powerful therapeutic approach towards the treatment and/or prevention of sickle cell disease. In vitro studies have shown that Clotrimazole, an imidazole-containing antimycotic agent, blocks $Ca^{2+}$-activated $K^+$ transport and cell dehydration in sickle erythrocytes (Brugnara et al., 1993, *J. Clin. Invest.* 92:520-526). Studies in a transgenic mouse model for sickle cell disease (SAD mouse, Trudel et al., 1991, *EMBO J.* 11:3157-3165) show that oral administration of Clotrimazole leads to inhibition of the red cell Gardos channel, increased red cell $K^+$ content, a decreased mean cell hemoglobin concentration (MCHC) and decreased cell density (De Franceschi et al., 1994, *J. Clin. Invest.* 93:1670-1676). Moreover, therapy with oral Clotrimazole induces inhibition of the Gardos channel and reduces erythrocyte dehydration in patients with sickle cell disease (Brugnara et al., 1996, *J. Clin. Invest.* 97:1227-1234). Other antimycotic agents which inhibit the Gardos channel in vitro include miconazole, econazole, butoconazole, oxiconazole and sulconazole (U.S. Pat. No. 5,273,992 to Brugnara et al.). All of these compounds contain an imidazole-like ring, i.e., a heteroaryl ring containing two or more nitrogens.

Also as discussed in the Background section, the modulation of early ionic mitogenic signals and inhibition of cell proliferation are powerful therapeutic approaches towards the treatment and/or prevention of disorders characterized by abnormal cell proliferation. It has been shown that Clotrimazole, in addition to inhibiting the Gardos channel of erythrocytes, also modulates ionic mitogenic signals and inhibits cell proliferation both in vitro and in vivo.

For example, Clotrimazole inhibits the rate of cell proliferation of normal and cancer cell lines in a reversible and dose-dependent manner in vitro (Benzaquen et al., 1995 *Nature Medicine* 1:534-540). Clotrimazole also depletes the intracellular $Ca^{2+}$ stores and prevents the rise in cystolic $Ca^{2+}$ that normally follows mitogenic stimulation. Moreover, in mice with severe combined immunodeficiency disease (SCID) and inoculated with MM-RU human melanoma cells, daily administration of Clotrimazole resulted in a significant reduction in the number of lung metastases observed (Benzaquen et al., supra).

It has now been discovered that substituted 3,3-diphenyl indanone, indane and (3-H) indole compounds, as well as analogues of these classes of compounds, also inhibit the Gardos channel of erythrocytes and/or mammalian cell proliferation. Thus, in one aspect, the present invention provides a new class of organic compounds that are capable of inhibiting the $Ca^{2+}$-activated potassium channel (Gardos channel) of erythrocytes, particularly sickle erythrocytes and/or of inhibiting mammalian cell proliferation, particularly mitogen-induced cell proliferation.

The activities of these compounds are quite surprising. Significantly, the compounds of the invention do not contain an imidazole or imidazole-like moiety. The imidazole or imidazole-like moiety is well-recognized as the essential functionality underlying the antimycotic and other biological activities of Clotrimazole and the other above-mentioned antimycotic agents. Thus, the substituted 3,3-diphenyl indanone, indane or (3-H) indole compounds and analogues of the invention provide an entirely new class of compounds capable of effecting inhibition of the Gardos channel and/or mammalian cell proliferation.

In another aspect, the invention provides a method of reducing sickle cell dehydration and/or delaying the occurrence of erythrocyte sickling in situ as a therapeutic approach towards the treatment of sickle cell disease. In its broadest sense, the method involves only a single step—the administration of at least one pharmacologically active compound of the invention, or a composition thereof, to a sickle erythrocyte in situ in an amount effective to reduce dehydration and/or delay the occurrence of cell sickling or deformation.

While not intending to be bound by any particular theory, it is believed that administration of the active compounds described herein in appropriate amounts to sickle erythrocytes in situ causes nearly complete inhibition of the Gardos channel of sickle cells, thereby reducing the dehydration of sickle cells and/or delaying the occurrence of cell sickling or deformation. In a preferred embodiment, the dehydration of a sickle cell is reduced and/or the occurrence of sickling is delayed in a sickle cell that is within the microcirculation vasculature of the subject, thereby reducing or eliminating the vaso-occlusion that is commonly caused by sickled cells.

Based in part on the surmised importance of the Gardos channel as a therapeutic target in the treatment of sickle cell disease, the invention is also directed to methods of treating or preventing sickle cell disease. In the method, an effective amount of one or more compounds according to the invention, or a pharmaceutical composition thereof, is administered to a patient suffering from sickle cell disease. The methods may be used to treat sickle cell disease prophylactically to decrease intracellular Hb S concentration and/or polymerization, and thus diminish the time and duration of red cell sickling and vaso-occlusion in the blood circulation. The methods may also be used therapeutically in patients with acute sickle cell crisis, and in patients suffering chronic sickle cell episodes to control both the frequency and duration of the crises.

The compounds of the invention are also potent, specific inhibitors of mammalian cell proliferation. Thus, in another aspect, the invention provides methods of inhibiting mammalian cell proliferation as a therapeutic approach towards the treatment or prevention of diseases characterized by unwanted or abnormal cell proliferation. In its broadest sense, the method involves only a single step—the administration of an effective amount of at least one pharmacologically active compound according to the invention to a mammalian cell in situ. The compound may act cytostatically, cytotoxically, or by a combination of both mechanisms to inhibit cell proliferation. Mammalian cells treatable in this manner include vascular smooth muscle cells, fibroblasts, endothelial cells, various pre-cancer cells and various cancer cells. In a preferred embodiment, cell proliferation is inhibited in a subject suffering from a disorder that is characterized by unwanted or abnormal cell proliferation. Such diseases are described more fully below.

Based in part on the surmised role of mammalian cell proliferation in certain diseases, the invention is also directed to methods of treating or preventing diseases characterized by abnormal cell proliferation. In the method, an effective amount of at least one compound according to the invention, or a pharmaceutical composition thereof, is administered to a patient suffering from a disorder that is characterized by abnormal cell proliferation. While not intending to be bound by any particular theory, it is believed that administration of an appropriate amount of a compound according to the invention to a subject inhibits cell proliferation by altering the ionic fluxes associated with early mitogenic signals. Such alteration of ionic fluxes is thought to be due to the ability of the compounds of the invention to inhibit potassium channels of cells, particularly $Ca^{2+}$-activated potassium channels. The method can be used prophylactically to prevent unwanted or abnormal cell proliferation, or may be used therapeutically to reduce or arrest proliferation of abnormally proliferating cells. The compound, or a pharmaceutical formulation thereof, can be applied locally to proliferating cells to arrest or inhibit proliferation at a desired time, or may be administered to a subject systemically to arrest or inhibit cell proliferation.

Diseases which are characterized by abnormal cell proliferation that can be treated or prevented by means of the present invention include blood vessel proliferative disorders, fibrotic disorders, arteriosclerotic disorders and various cancers.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferative disorders include arthritis, where new capillary blood vessels invade the joint and destroy cartilage and ocular diseases such as diabetic retinopathy, where new capillaries in the retina invade the vitreous, bleed and cause blindness and neovascular glaucoma.

Another example of abnormal neovascularization is that associated with solid tumors. It is now established that unrestricted growth of tumors is dependent upon angiogenesis and that induction of angiogenesis by liberation of angiogenic factors can be an important step in carcinogenesis. For example, basic fibroblast growth factor (bFGF) is liberated by several cancer cells and plays a crucial role in cancer angiogenesis. The demonstration that certain animal tumors regress when angiogenesis is inhibited has provided the most compelling evidence for the role of angiogenesis in tumor growth. Other cancers that are associated with neovascularization include hemangioendotheliomas, hemangiomas and Kaposi's sarcoma.

Proliferation of endothelial and vascular smooth muscle cells is the main feature of neovascularization. The invention is useful in inhibiting such proliferation, and therefore in inhibiting or arresting altogether the progression of the angiogenic condition which depends in whole or in part upon such neovascularization. The invention is particularly useful when the condition has an additional element of endothelial or vascular smooth muscle cell proliferation that is not necessarily associated with neovascularization. For example, psoriasis may additionally involve endothelial cell proliferation that is independent of the endothelial cell proliferation associated with neovascularization. Likewise, a solid tumor which requires neovascularization for continued growth may also be a tumor of endothelial or vascular smooth muscle cells. In this case, growth of the tumor cells themselves, as well as the neovascularization, is inhibited by the compounds described herein.

The invention is also useful for the treatment of fibrotic disorders such as fibrosis and other medical complications of fibrosis which result in whole or in part from the proliferation of fibroblasts. Medical conditions involving fibrosis (other than atherosclerosis, discussed below) include undesirable tissue adhesion resulting from surgery or injury.

Other cell proliferative disorders which can be treated by means of the invention include arteriosclerotic conditions. Arteriosclerosis is a term used to describe a thickening and hardening of the arterial wall. An arteriosclerotic condition as used herein means classical atherosclerosis, accelerated atherosclerosis, atherosclerotic lesions and any other arteriosclerotic conditions characterized by undesirable endothelial and/or vascular smooth muscle cell proliferation, including vascular complications of diabetes.

Proliferation of vascular smooth muscle cells is a main pathological feature in classical atherosclerosis. It is believed that liberation of growth factors from endothelial cells stimulates the proliferation of subintimal smooth muscle which, in turn, reduces the caliber and finally obstructs the artery. The invention is useful in inhibiting such proliferation, and therefore in delaying the onset of, inhibiting the progression of, or even halting the progression of such proliferation and the associated atherosclerotic condition.

Proliferation of vascular smooth muscle cells produces accelerated atherosclerosis, which is the main reason for failure of heart transplants that are not rejected. This proliferation is also believed to be mediated by growth factors, and can ultimately result in obstruction of the coronary arteries. The invention is useful in inhibiting such obstruction and reducing the risk of, or even preventing, such failures.

Vascular injury can also result in endothelial and vascular smooth muscle cell proliferation. The injury can be caused by any number of traumatic events or interventions, including vascular surgery and balloon angioplasty. Restenosis is the main complication of successful balloon angioplasty of the coronary arteries. It is believed to be caused by the release of growth factors as a result of mechanical injury to the endothelial cells lining the coronary arteries. Thus, by inhibiting unwanted endothelial and smooth muscle cell proliferation, the compounds described herein can be used to delay, or even avoid, the onset of restenosis.

Other atherosclerotic conditions which can be treated or prevented by means of the present invention include diseases of the arterial walls that involve proliferation of endothelial and/or vascular smooth muscle cells, such as complications of diabetes, diabetic glomerulosclerosis and diabetic retinopathy.

The compounds described herein are also potent antineoplastic agents and are therefore useful in treating or preventing various types of neoplastic diseases. Neoplastic diseases which can be treated by means of the present invention include, but are not limited to, biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute and chronic lymphocytic and myelogenous leukemia, multiple myeloma, AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma (teratomas, choriocarcinomas)), stromal tumors and germ cell tumors; thyroid cancer, including thyroid adenocarcinoma and medullar carcinoma; and renal cancer including adenocarcinoma and Wilms tumor.

The compounds of the invention are useful with hormone dependent and also with nophormone dependent cancers. They also are useful with prostate and breast cancers. They further are useful with multidrug resistant strains of cancer.

In addition to the particular disorders enumerated above, the invention is also useful in treating or preventing dermatological diseases including keloids, hypertrophic scars, seborrheic dermatosis, papilloma virus infection (e.g., producing verruca vulgaris, verruca plantaris, verruca plan, condylomata, etc.), eczema and epithelial precancerous lesions such as actinic keratosis; other inflammatory diseases including proliferative glomerulonephritis; lupus erythematosus; scleroderma; temporal arthritis; thromboangiitis obliterans; mucocutaneous lymph node syndrome; and other pathologies mediated by growth factors including uterine leiomyomas.

The compounds and methods of the invention provide myriad advantages over agents and methods commonly used to treat sickle cell disease and/or cell proliferative disorders. The compounds and methods of the invention also provide myriad advantages over the treatment of sickle cell disease and/or cell proliferative disorders with Clotrimazole or other antimycotic agents. Most significantly, the compounds of the invention have reduced toxicity as compared with Clotrimazole and other antimycotic agents, and therefore provide consequential therapeutic benefits in clinical settings. For example, for clotrimazole, it is well-known that the imidazole moiety is responsible for inhibiting a wide range of cytochrome P-450 isozyme catalyzed reactions, which constitutes their main toxicological effects (Pappas and Franklin, 1993, *Toxicology* 80:27-35; Matsuura et al., 1991, *Biochemical Pharmacology* 41:1949-1956). The compounds of the invention do not contain an imidazole or imidazole-like moiety and therefore may not share Clotrimazole's known toxicities.

5.1 The Compounds

The compounds which are capable of inhibiting the Gardos channel and/or mammalian cell proliferation according to the invention are generally substituted 3,3-diphenyl indanone, indane and (3-H) indole compounds, as well as analogues of these classes of compounds wherein the atoms at ring positions 1 and 2 are connected via a double bond.

In one illustrative embodiment, the compounds capable of inhibiting the Gardos channel and/or mammalian cell proliferation according to the invention are compounds having the structural formula:

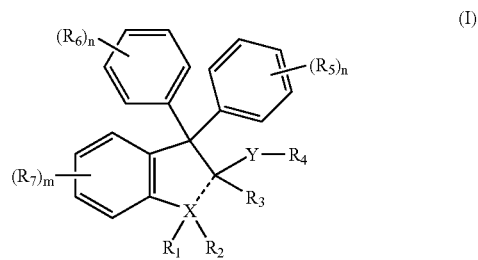

(I)

or pharmaceutically acceptable salts or hydrates thereof, wherein:

m is 0, 1, 2, 3 or 4;

each n is independently 0, 1, 2, 3, 4 or 5;

X is C or N;

Y is absent, $(C_1-C_6)$ alkyl, $(C_1-C_6)$ alkenyl or $(C_1-C_6)$ alkynyl;

$R_1$ is absent, —OR, —SR, =O, =S, =N—OR, —O—C(O)R, —S—C(O)R, —O—C(S)R, —S—C(S)R, or when taken together with $R_2$ is a 3-8 membered heterocycloalkyl or a substituted 3-8 membered heterocycloalkyl;

$R_2$ is absent or —H;

$R_3$ is absent or —H;

$R_4$ is —H, —OR', —SR', —NR'$_2$, —CN, —NO$_2$, $(C_3-C_8)$ cycloalkyl, 3-8 membered heterocycloalkyl, —C(O)R', —C(S)R', —C(O)OR', —C(S)OR', —C(O)SR', —C(S)SR', —C(O)NR'$_2$ or —C(S)NR'$_2$;

each $R_5$, $R_6$ and $R_7$ is independently selected from the group consisting of -halogen, —R', —OR', —SR', —NR'$_2$, —ONR'$_2$, —SNR'$_2$, —NO$_2$, —CN, —C(O)R', —C(S)R', —C(O)OR', —C(O)SR', —C(S)OR', —CS(S)R', —C(O)NR'$_2$, —C(S)NR'$_2$, —C(O)NR'(OR'), —C(S)NR'(OR'); —C(O)NR'(SR'), —C(S)NR'(SR'), —CH(CN)$_2$, —CH[C(O)R']$_2$, —CH[C(S)R']$_2$, —CH[C(O)OR']$_2$, —CH[C(S)OR']$_2$, —CH[C(O)SR']$_2$ and —CH[C(S)SR']$_2$;

each R is independently selected from the group consisting of —H, $(C_1-C_6)$ alkyl, $(C_1-C_6)$ alkenyl, $(C_1-C_6)$ alkynyl, $(C_5-C_{20})$ aryl, substituted $(C_5-C_{20})$ aryl, $(C_6-C_{26})$ alkaryl and substituted $(C_6-C_{26})$ alkaryl;

the heterocycloalkyl substituents are each independently selected from the group consisting of —CN, —NO$_2$, —NR'$_2$, —OR', —C(O)NR'$_2$, —C(S)NR'$_2$, —C(O)OR', —C(S)OR', —C(O)SR', —C(S)SR' and trihalomethyl;

the aryl and alkaryl substituents are each independently selected from the group consisting of halogen, —C(O)R', —C(S)R', —C(O)OR', —C(S)OR', —C(O)SR', —C(S)SR', —C(O)NR'$_2$, —C(S)NR'$_2$ and trihalomethyl;

each R' is independently selected from the group consisting of —H, $(C_1-C_6)$ alkyl, $(C_1-C_6)$ alkenyl and $(C_1-C_6)$ alkynyl; and

- - - designates a single or double bond.

In the compounds of structural formula (I), the bond between the atoms at ring positions 1 and 2 (designated - - -) can be either a single or double bond. It will be recognized by those of skill in the art that when the bond is a double bond, certain of the substituents must be absent. It will also be recognized that the identity of X also influences the presence or absence of certain substituents. Thus, it is to be understood that when X is N and - - - is a double bond, $R_1$, $R_2$ and $R_3$ are absent; when X is C and - - - is a double bond, $R_2$ and $R_3$ are absent. When X is N and - - - is a single bond, one of $R_1$ and $R_2$ is present and the other is absent and $R_3$ is present; when X is C and - - - is a single bond, $R_1$, $R_2$ and $R_3$ are each present.

In a preferred embodiment of the invention, the chalcogens in the compounds of formula (I) are each oxygen.

In another preferred embodiment of the invention, the compounds are those of structural formula (I) wherein:
  m is 0, 1, 2, 3 or 4;
  each n is independently 0, 1, 2, 3, 4 or 5;
  X is C or N;
  Y is absent, $(C_1-C_6)$ alkyl, $(C_1-C_6)$ alkenyl or $(C_1-C_6)$ alkynyl;
  $R_1$ is absent, —OR, =O, =N—OR, —O—C(O)R, or when taken together with $R_2$ is a 3-8 membered oxirane or a substituted 3-8 membered oxirane;
  $R_2$ is absent or —H;
  $R_3$ is absent or —H;
  $R_4$ is —H, —OR', —NR'$_2$, —CN, —NO$_2$, $(C_3-C_9)$ cycloalkyl, 3-8 membered oxiranyl, 5-8 membered dioxycycloalkyl, —C(O)R', —C(O)OR' or —C(O)NR'$_2$;
  each $R_5$, $R_6$ and $R_7$ is independently selected from the group consisting of -halogen, —R', —OR', —NR'$_2$, —ONR'$_2$, —NO$_2$, —CN, —C(O)R', —C(O)OR', —C(O)NR'$_2$, —C(O)NR'(OR'), —CH(CN)$_2$, —CH[C(O)R']$_2$ and —CH[C(O)OR']$_2$;
  each R is independently selected from the group consisting of —H, $(C_1-C_6)$ alkyl, $(C_1-C_6)$ alkenyl, $(C_1-C_6)$ alkynyl, $(C_5-C_{20})$ aryl, substituted $(C_5-C_{20})$ aryl, $(C_6-C_{26})$ alkaryl and substituted $(C_6-C_{26})$ alkaryl;
  the oxirane substituents are each independently selected from the group consisting of —CN, —NO$_2$, —NR'$_2$, —OR', —C(O)NR'$_2$, —C(O)OR' and trihalomethyl;
  the aryl and alkaryl substituents are each independently selected from the group consisting of halogen, —C(O)R', —C(O)OR', —C(O)NR'$_2$ and trihalomethyl;
  each R' is independently selected from the group consisting of —H, $(C_1-C_6)$ alkyl, $(C_1-C_6)$ alkenyl and $(C_1-C_6)$ alkynyl; and/or
  - - - designates a single or double bond.

In another preferred embodiment, the compounds are those of structural formula (I) wherein:
  m is 0 or 1;
  each n is independently 0 or 1;
  X is C or N;
  Y is absent, $(C_1-C_3)$ alkyl, $(C_1-C_3)$ alkenyl or $(C_1-C_3)$ alkynyl;
  $R_1$ is absent —H, —OR, =O, —NR$_2$, =N—OR, —O—C(O)R, or when taken together with $R_2$ is 3-5 membered oxirane or 3-5 membered substituted oxirane;
  $R_2$ is absent or —H;
  $R_3$ is absent or —H;
  $R_4$ is —H, —OR, —NR$_2$, —CN, —C(O)OR, —C(O)NR$_2$ or 5-6 membered dioxoycycloalkyl;
  each $R_5$, $R_6$ and $R_7$ is independently selected from the group consisting of —R', —F, —Cl or —Br;

each R is independently selected from the group consisting of —H, $(C_1-C_3)$ alkyl, $(C_1-C_3)$ alkenyl, $(C_1-C_3)$ alkynyl, $(C_5-C_{10})$ aryl, substituted $(C_5-C_{10})$ aryl, $(C_6-C_{13})$ alkaryl, substituted $C_6-C_{13})$ alkaryl;
  the oxirane substituent is —CN, —NO$_2$, —NR'$_2$, —OR' and trihalomethyl;
  the aryl and alkaryl substituents are each independently selected from the group consisting of —F, —Cl, —Br, —CN, —NO$_2$, —NR'$_2$, —C(O)R', —C(O)OR' and trihalomethyl;
  R' is —H, $(C_1-C_3)$ alkyl, $(C_1-C_3)$ alkenyl or $(C_1-C_3)$ alkynyl; and/or
  - - - is a single or double bond.

In still another preferred embodiment, the compounds are those of structural formula (I) wherein:
  m is 0, 1, 2, 3 or 4;
  each n is independently 0, 1, 2, 3, 4 or 5;
  X is C or N;
  Y is absent, $(C_1-C_6)$ alkyl, $(C_1-C_6)$ alkenyl or $(C_1-C_6)$ alkynyl;
  $R_1$ is absent, —OR, —SR, =O, =S, =N—OR, —O—C(O)R, —S—C(O)R, —O—C(S)R, —S—C(S)R, or when taken together with $R_2$ is a 3-8 membered heterocycloalkyl or a substituted 3-8 membered heterocycloalkyl;
  $R_2$ is absent or —H;
  $R_3$ is absent or —H;
  $R_4$ is —H, —OR', —SR', —NR'$_2$, —CN, —NO$_2$, $(C_3-C_8)$ cycloalkyl, 3-8 membered heterocycloalkyl, —C(O)R', —C(S)R', —C(O)OR', —C(S)OR', —C(O)SR', —C(S)SR', —C(O)NR'$_2$ or —C(S)NR'$_2$;
  each $R_5$, $R_6$ and $R_7$ is independently selected from the group consisting of -halogen, —R', —OR', —SR', —NR'$_2$, —ONR'$_2$, —SNR'$_2$, —NO$_2$, —CN, —C(O)R', —C(S)R', —C(O)OR', —C(O)SR', —C(S)OR', —CS(S)R', —C(O)NR'$_2$, —C(S)NR'$_2$, —C(O)NR'(OR'), —C(S)NR'(OR'); —C(O)NR'(SR'), —C(S)NR'(SR'), —CH(CN)$_2$, —CH[C(O)R']$_2$, —CH[C(S)R']$_2$, —CH[C(O)OR']$_2$, —CH[C(S)OR']$_2$, —CH[C(O)SR']$_2$ and —CH[C(S)SR']$_2$;
  each R is independently selected from the group consisting of —H, $(C_1-C_6)$ alkyl, $(C_1-C_6)$ alkenyl, $(C_1-C_6)$ alkynyl, $(C_5-C_{20})$ aryl, substituted $(C_5-C_{20})$ aryl, $(C_6-C_{26})$ alkaryl and substituted $(C_6-C_{26})$ alkaryl;
  the heterocycloalkyl substituents are each independently selected from the group consisting of —CN, —NO$_2$, —NR'$_2$, —OR', —C(O)NR'$_2$, —C(S)NR'$_2$, —C(O)OR', —C(S)OR', —C(O)SR', —C(S)SR' and trihalomethyl;
  the aryl and alkaryl substituents are each independently selected from the group consisting of halogen, —C(O)R', —C(S)R', —C(O)OR', —C(S)OR', —C(O)SR', —C(S)SR', —C(O)NR'$_2$, —C(S)NR'$_2$ and trihalomethyl;
  each R' is independently selected from the group consisting of —H, $(C_1-C_6)$ alkyl, $(C_1-C_6)$ alkenyl and $(C_1-C_6)$ alkynyl;
  - - - designates a single or double bond; and
  wherein when X is C and $R_1$ is =O, =S or —OR', at least one of $R_5$, $R_6$ or $R_7$ is other than —R', preferably other than —H, or Y is present or $R_4$ is other than —H; and when X is N, - - - is a double bond and $R_1$, $R_2$, $R_3$ and Y are absent, $R_4$ is other than —NR'$_2$, preferably other than —NH$_2$.

In still another preferred embodiment, the compounds are those of structural formula (I) wherein:
  m is 0, 1, 2, 3 or 4;
  each n is independently 0, 1, 2, 3, 4 or 5;
  X is C;
  Y is absent, $(C_1-C_6)$ alkyl, $(C_1-C_6)$ alkenyl or $(C_1-C_6)$ alkynyl;

$R_1$ is absent, —OR, —SR, =O, =S, =N—OR, —O—C(O)R, —S—C(O)R, —O—C(S)R, —S—C(S)R, or when taken together with $R_2$ is a 3-8 membered heterocycloalkyl or a substituted 3-8 membered heterocycloalkyl;

$R_2$ is absent or —H;

$R_3$ is absent or —H;

$R_4$ is —H, —OR', —SR', —NR'$_2$, —CN, —NO$_2$, ($C_3$-$C_8$) cycloalkyl, 3-8 membered heterocycloalkyl, —C(O)R', —C(S)R', —C(O)OR', —C(S)OR', —C(O)SR', —C(S)SR', —C(O)NR'$_2$ or —C(S)NR'$_2$;

each $R_5$, $R_6$ and $R_7$ is independently selected from the group consisting of -halogen, —R', —OR', —SR', —NR'$_2$, —ONR'$_2$, —SNR'$_2$, —NO$_2$, —CN, —C(O)R', —C(S)R', —C(O)OR', —C(O)SR', —C(S)OR', —CS(S)R', —C(O)NR'$_2$, —C(S)NR'$_2$, —C(O)NR'(OR'), —C(S)NR'(OR'); —C(O)NR'(SR'), —C(S)NR'(SR'), —CH(CN)$_2$, —CH[C(O)R']$_2$, —CH[C(S)R']$_2$, —CH[C(O)OR']$_2$, —CH[C(S)OR']$_2$, —CH[C(O)SR']$_2$ and —CH[C(S)SR']$_2$;

each R is independently selected from the group consisting of —H, ($C_1$-$C_6$) alkyl, ($C_1$-$C_6$) alkenyl, ($C_1$-$C_6$) alkynyl, ($C_5$-$C_{20}$) aryl, substituted ($C_5$-$C_{20}$) aryl, ($C_6$-$C_{26}$) alkaryl and substituted ($C_6$-$C_{26}$) alkaryl;

the heterocycloalkyl substituents are each independently selected from the group consisting of —CN, —NO$_2$, —NR'$_2$, —OR', —C(O)NR'$_2$, —C(S)NR'$_2$, —C(O)OR', —C(S)OR', —C(O)SR', —C(S)SR' and trihalomethyl;

the aryl and alkaryl substituents are each independently selected from the group consisting of halogen, —C(O)R', —C(S)R', —C(O)OR', —C(S)OR', —C(O)SR', —C(S)SR', —C(O)NR'$_2$, —C(S)NR'$_2$ and trihalomethyl;

each R' is independently selected from the group consisting of —H, ($C_1$-$C_6$) alkyl, ($C_1$-$C_6$) alkenyl and ($C_1$-$C_6$) alkynyl;

- - - designates a single or double bond; and wherein when $R_1$ is =O or —OH, at least one of $R_5$, $R_6$ or $R_7$ is other than —R', preferably other than —H, or Y is present or $R_4$ is other than —H.

In still another preferred embodiment, the compounds of structural formula (I) are selected from the group of compounds set forth below:

(1)
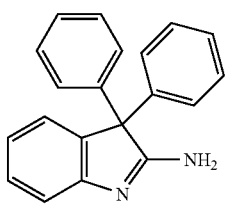

(2)
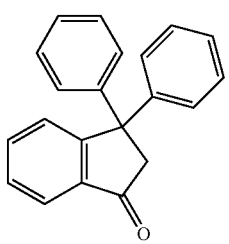

(3)
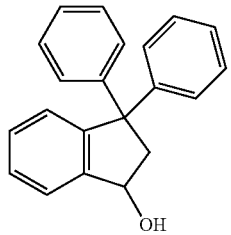

(4)
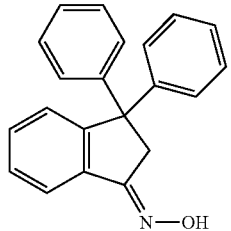

(5)
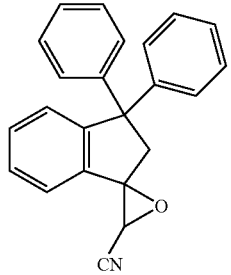

(6)
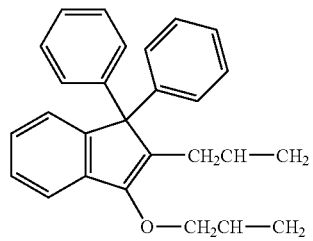

(7)
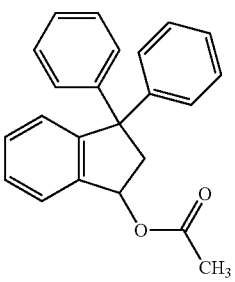

(8)
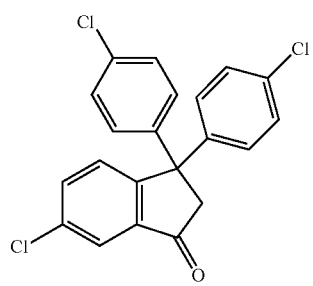

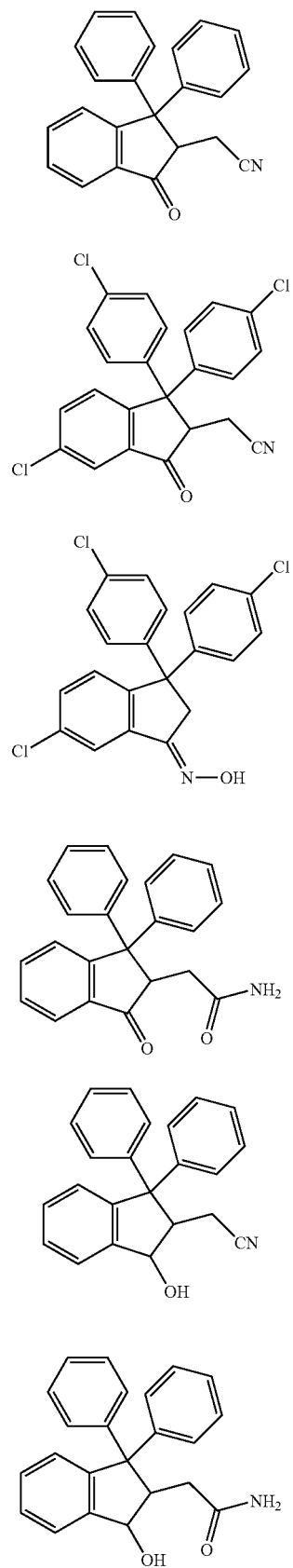
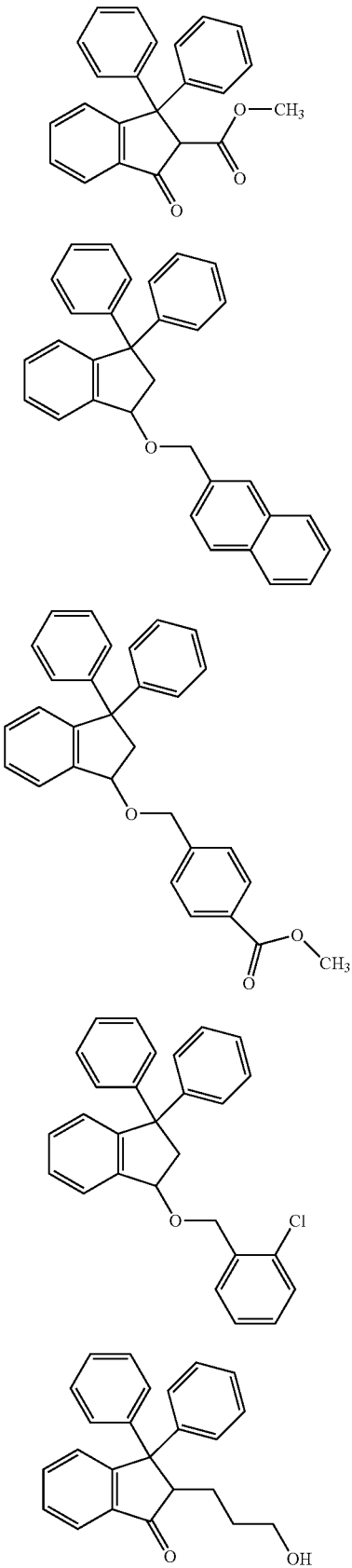

-continued

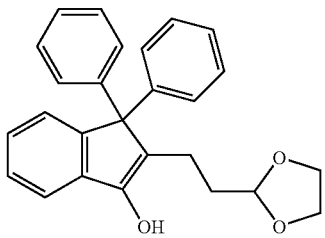

(20)

In still another preferred embodiment, the compounds of structural formula (I) are selected from the group consisting of Compounds 4, 5, 6, 7, 8, 9, 10, 11, 12, 13, 14, 15, 16, 17, 18, 19 and 20.

The chemical structural formulae referred to herein may exhibit the phenomena of tautomerism, conformational isomerism, stereoisomerism or geometric isomerism. As the structural formulae drawings within this specification can represent only one of the possible tautomeric, conformational isomeric, enantiomeric or geometric isomeric forms, it should be understood that the invention encompasses any tautomeric, conformational isomeric, enantiomeric or geometric isomeric forms which exhibit biological or pharmacological activity as described herein.

The compounds of the invention may be in the form of free acids, free bases or pharmaceutically effective salts thereof. Such salts can be readily prepared by treating a compound with an appropriate acid. Such acids include, by way of example and not limitation, inorganic acids such as hydrohalic acids (hydrochloric, hydrobromic, etc.), sulfuric acid, nitric acid, phosphoric acid, etc.; and organic acids such as acetic acid, propanoic acid, 2-hydroxyacetic acid, 2-hydroxypropanoic acid, 2-oxopropanoic acid, propandioic acid, butandioic acid, etc. conversely, the salt can be converted into the free base form by treatment with alkali.

In addition to the above-described compounds and their pharmaceutically acceptable salts, the invention may employ, where applicable, solvated as well as unsolvated forms of the compounds (e.g., hydrated forms).

The compounds described herein may be prepared by any processes known to be applicable to the preparation of chemical compounds. Suitable processes are well known in the art. Preferred processes are illustrated by the representative examples. Necessary starting materials may be obtained commercially or by standard procedures of organic chemistry. Moreover, many of the compounds are commercially available.

An individual compound's relevant activity and potency as an agent to affect sickle cell dehydration or deformation and/or mammalian cell proliferation may be determined using standard techniques. Preferentially, a compound is subject to a series of screens to determine its pharmacological activity.

In most cases, the active compounds of the invention exhibit two pharmacological activities: inhibition of the Gardos channel of erythrocytes and inhibition of mammalian cell proliferation. However, in some cases, the compounds of the invention may exhibit only one of these pharmacological activities. Any compound encompassed by structural formula (I) which exhibits at least one of these pharmacological activities is considered to be within the scope of the present invention.

In general, the active compounds of the invention are those which induce at least about 25% inhibition of the Gardos channel of erythrocytes (measured at about 10 µM) and/or about 25% inhibition of mammalian cell proliferation (measured at about 10 µM), as measured using in vitro assays that are commonly known in the art (see, e.g., Brugnara et al., 1993, *J. Biol. Chem.* 268(12):8760-8768; Benzaquen et al., 1995, *Nature Medicine* 1:534-540). Alternatively, or in addition, the active compounds of the invention generally will have an $IC_{50}$ (concentration of compound that yields 50% inhibition) for inhibition of the Gardos channel of less than about 10 µM and/or an $IC_{50}$ for inhibition of cell proliferation of less than about 10 µM, as measured using in vitro assays that are commonly known in the art (see, e.g., Brugnara et al., 1993, *J. Biol. Chem.* 268(12):8760-8768; Benzaquen et al., 1995, *Nature Medicine* 1:534-540).

Representative active compounds according to the invention are Compounds 1 through 20, as illustrated above.

In certain embodiments of the invention, compounds which, exhibit only one pharmacological activity, or a higher degree of one activity, may be preferred. Thus, when the compound is to be used in methods to treat or prevent sickle cell disease, or in methods to reduce sickle cell dehydration and/or delay the occurrence of erythrocyte sickling or deformation in situr it is preferred that the compound exhibit at least about 75% Gardos channel inhibition (measured at about 10 µM) and/or have an $IC_{50}$ of Gardos channel inhibition of less than about 1 µM, with at least about 90% inhibition and/or an $IC_{50}$ of less than about 0.1 µM being particularly preferred.

Exemplary preferred compounds for use in methods related to Gardos channel inhibition and sickle cell disease include compound numbers 1, 2, 3, 4, 7, 9, 12, 13 and 14.

When the compound is to be used in methods to treat or prevent disorders characterized by abnormal cell proliferation or in methods to inhibit cell proliferation in situ, it is preferable that the compound exhibit at least about 75% inhibition of mitogen-induced cell proliferation (measured at about 10 µM) and/or have an $IC_{50}$ of cell proliferation of less than about 3.5 µM, with at least about 90% inhibition and/or an $IC_{50}$ of less than about 1 µM being particularly preferred.

Exemplary preferred compounds for use in methods inhibiting mammalian cell proliferation or for the treatment or prevention of diseases characterized by abnormal cell proliferation include compound numbers 1, 2, 3, 4, 6, 7, 8, 10, 11, 15, 16, 17, 19 and 20.

5.2 Formulation and Routes of Administration

The compounds described herein, or pharmaceutically acceptable addition salts or hydrates thereof, can be delivered to a patient using a wide variety of routes or modes of administration. Suitable routes of administration include, but are not limited to, iphalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from sickle cell disease, the compounds of the invention can be administered in cocktails containing agents used to treat the pain, infection and other symptoms and side effects commonly associated with sickle cell disease. Such agents include, e.g., analgesics, antibiotics, etc. The compounds can also be administered in cocktails containing other agents that are commonly used to treat sickle cell disease, including butyrate and butyrate derivatives (Perrine et al., 1993, *N. Engl. J. Med*. 328(2):81-86); hydroxyurea (Charache et al., 1995, *N. Engl. J. Med*. 323(20):1317-1322); erythropoietin (Goldberg et al, 1990, *N. Engl. J. Med*. 323(6): 366-372); and dietary salts such as magnesium (De Franceschi et al., 1996, *Blood* 88(648a):2580).

When administered to a patient undergoing cancer treatment, the compounds may be administered in cocktails containing other anti-cancer agents and/or supplementary potentiating agents. The compounds may also be administered in cocktails containing agents that treat the side-effects of radiation therapy, such as anti-emetics, radiation protectants, etc.

Anti-cancer drugs that can be co-administered with the compounds of the invention include, e.g., Aminoglutethimide; Asparaginase; Bleomycin; Busulfan; Carboplatin; Carmustine (BCNU); Chlorambucil; Cisplatin (cis-DDP); Cyclophosphamide; CytarabineHCl; Dacarbazine; Dactinomycin; Daunorubicin HCl; Doxorubicin HCl; Estramustine phosphate sodium; Etoposide (VP-16); Floxuridine; Fluorouracil (5-FU); Flutamide; Hydroxyurea (hydroxycarbamide); Ifosfamide; Interferon Alfa-2a, Alfa 2b, Lueprolide acetate (LHRH-releasing factor analogue); Lomustine (CCNU); Mechlorethamine HCl (nitrogen mustard); Melphalan; Mercaptopurine; Mesna; Methotrexate (MTX); Mitomycin; Mitotane (o.p'-DDD); Mitoxantrone HCl; octreotide; Plicamycin; Procarbazine HCl; Streptozocin; Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bis-guanylhydrazone; MGBG); Pentostatin; Semustine (methyl-CCNU); Teniposide (VM-26); paclitaxel and other taxanes; and Vindesine sulfate.

Supplementary potentiating agents that can be co-administered with the compounds of the invention include, e.g., Tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{++}$ antagonists (e.g., verapamil, nifedipine, nitrendipine and caroverine); Amphotericin (e.g., Tween 80 and perhexiline maleate); Triparanol analogues (e.g., tamoxifen); antiarrhythmic drugs (e.g., quinidine); antihypertensive drugs (e.g., reserpine); Thiol depleters (e.g., buthionine and sulfoximine); and calcium leucovorin.

The active compound(s) may be administered per se or in the form of a pharmaceutical composition wherein the active compound(s) is in admixture with one or more pharmaceutically acceptable carriers, excipients or diluents. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration the compositions may take the form of tablets or lozenges formulated in conventional manner.

For administration by iphalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an iphaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and Polymers such as polyethylene glycols.

5.3 Effective Dosages

Pharmaceutical compositions suitable for use with the present invention include compositions wherein the active ingredient is contained in a therapeutically effective amount, i.e., in an amount effective to achieve its intended purpose. Of course, the actual amount effective for a particular application will depend, inter aria, on the condition being treated. For example, when administered in methods to reduce sickle cell dehydration and/or delay the occurrence of erythrocyte sickling or distortion in situ, such compositions will contain an amount of active ingredient effective to achieve this result. When administered in methods to inhibit cell proliferation, such compositions will contain an amount of active ingredient effective to achieve this result. When administered to patients suffering from sickle cell disease or disorders characterized by abnormal cell proliferation, such compositions will contain an amount of active ingredient effective to, inter alia, prevent the development of or alleviate the existing symptoms of, or prolong the survival of, the patient being treated. For use in the treatment of cancer, a therapeutically effective amount further includes that amount of compound or composition which arrests or regresses the growth of a tumor. Determination of an effective amount is well within the capabilities of those skilled in the art, especially in light of the detailed disclosure herein.

For any compound described herein the therapeutically effective amount can be initially determined from cell culture arrays. Target plasma concentrations will be those concentrations of active compound(s) that are capable of inducing at least about 25% inhibition of the Gardos channel and/or at least about 25% inhibition of cell proliferation in cell culture assays, depending, of course, on the particular desired application. Target plasma concentrations of active compound(s) that are capable of inducing at least about 50%, 75%, or even 90% or higher inhibition of the Gardos channel and/or cell proliferation in cell culture assays are preferred. The percentage of inhibition of the Gardos channel and/or cell proliferation in the patient can be monitored to assess the appropriateness of the plasma drug concentration achieved, and the dosage can be adjusted upwards or downwards to achieve the desired percentage of inhibition.

Therapeutically effective amounts for use in humans can also be determined from animal models. For example, a dose for humans can be formulated to achieve a circulating concentration that has been found to be effective in animals. A particularly useful animal model for sickle cell disease is the SAD mouse model (Trudel et al., 1991, *EMBO J.* 11:3157-3165). Useful animal models for diseases characterized by abnormal cell proliferation are well-known in the art. In particular, the following references provide suitable animal models for cancer xenografts (Corbett et al., 1996, *J. Exp. Ther. Oncol.* 1:95-108; Dykes et al., 1992, *Contrib. Oncol. Basel. Karger* 42:1-22), restenosis (Carter et al., 1994, *J. Am. Coll. Cardiol.* 24(5):1398-1405), atherosclerosis (Zhu et al., 1994, *Cardiology* 85(6):370-377) and neovascularization (Epstein et al., 1987, *Cornea* 6(4):250-257). The dosage in humans can be adjusted by monitoring Gardos channel inhibition and/or inhibition of cell proliferation and adjusting the dosage upwards or downwards, as described above.

A therapeutically effective dose can also be determined from human data for compounds which are known to exhibit similar pharmacological activities, such as Clotrimazble and other antimycotic agents (see, e.g., Brugnara et al., 1995, *JPET* 273:266-272; Benzaquen et al., 1995, *Nature Medicine* 1:534-540; Brugnara et al., 1996, *J. Clin. Invest.* 97(5):1227-1234). The applied dose can be adjusted based on the relative bioavailability and potency of the administered compound as compared with Clotrimazole.

Adjusting the dose to achieve maximal efficacy in humans based on the methods described above and other methods as are well-known in the art is well within the capabilities of the ordinarily skilled artisan.

Of course, in the case of local administration, the systemic circulating concentration of administered compound will not be of particular importance. In such instances, the compound is administered so as to achieve a concentration at the local area effective to achieve the intended result.

For use in the prophylaxis and/or treatment of sickle cell disease, including both chronic sickle cell episodes and acute sickle cell crisis, a circulating concentration of administered compound of about 0.001 µM to 20 µM is considered to be effective, with about 0.1 µM to 5 µM being preferred.

Patient doses for oral administration of the compounds described herein, which is the preferred mode of administration for prophylaxis and for treatment of chronic sickle cell episodes, typically range from about 80 mg/day to 16,000 mg/day, more typically from about 800 mg/day to 8000 mg/day, and most typically from about 800 mg/day to 4000 mg/day. Stated in terms of patient body weight, typical dosages range from about 1 to 200 mg/kg/day, more typically from about 10 to 100 mg/kg/day, and most typically from about 10 to 50 mg/kg/day. Stated in terms of patient body surface areas, typical dosages range from about 40 to 8000 mg/m$^2$/day, more typically from about 400 to 4000 mg/m$^2$/day, and most typically from about 400 to 2000 mg/m$^2$/day.

For use in the treatment of disorders characterized by abnormal cell proliferation, including cancer, arteriosclerosis and angiogenic conditions such as restenosis, a circulating concentration of administered compound of about 0.001 µM to 20 µM is considered to be effective, with about 0.1 µM to 5 µM being preferred.

Patient doses for oral administration of the compounds described herein for the treatment or prevention of cell proliferative disorders typically range from about 80 mg/day to 16,000 mg/day, more typically from about 800 mg/day to 8000 mg/day, and most typically from about 800 mg/day to 4000 mg/day. Stated in terms of patient body weight, typical dosages range from about 1 to 200 mg/kg/day, more typically from about 10 to 100 mg/kg/day, and most typically from about 10 to 50 mg/kg/day. Stated in terms of patient body surface areas, typical dosages range from about 40 to 8000 mg/m$^2$/day, more typically from about 400 to 4000 mg/m$^2$/day, and most typically from about 400 to 2000 mg/m$^2$/day.

For other modes of administration, dosage amount and interval can be adjusted individually to provide plasma levels of the administered compound effective for the particular clinical indication being treated. For example, if acute sickle crises are the most dominant clinical manifestation, a compound according to the invention can be administered in relatively high concentrations multiple times per day. Alternatively, if the patient exhibits only periodic sickle cell crises on an infrequent or periodic or irregular basis, it may be more desirable to administer a compound of the invention at minimal effective concentrations and to use a less frequent regimen of administration. This will provide a therapeutic regimen that is commensurate with the severity of the sickle cell disease state.

For use in the treatment of tumorigenic cancers, the compounds can be administered before, during or after surgical removal of the tumor. For example, the compounds can be administered to the tumor via injection into the tumor mass prior to surgery in a single or several doses. The tumor, or as much as possible of the tumor, may then be removed surgically. Further dosages of the drug at the tumor site can be applied post removal. Alternatively, surgical removal of as much as possible of the tumor can precede administration of the compounds at the tumor site.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the clinical symptoms demonstrated by the particular patient. of course, many factors are important in determining a therapeutic regimen suitable for a particular indication or patient. Severe indications such as cancer may warrant administration of higher dosages as compared with less severe indications such as sickle cell disease.

5.4 Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds which exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, In *The Pharmacological Basis of Therapeutics*, Ch. 1 p1).

The invention having been described, the following examples are intended to illustrate, not limit, the invention.

6. EXAMPLE

Compound Syntheses

This Example demonstrates general methods for synthesizing the compounds of the invention, as well as preferred methods of synthesizing certain exemplary compounds of the invention. In all of the reaction schemes described herein, suitable starting materials are either commercially available or readily obtainable using standard techniques of organic synthesis. Where necessary, suitable groups and schemes for protecting the various funtionalities are well-known in the art, and can be found, for example, in Kocienski, *Protecting Groups*, Georg Thieme Verlag, New York, 1994 and Greene & Wuts, *Protective Groups in Organic Chemistry*, John Wiley & Sons, New York, 1991.

In FIGS. 1 and 2, the various substituents are defined as for structure (I), supra.

6.1 Synthesis of Substituted 3.3-Diphenyl Indanones

Referring to FIG. 1, substituted 3,3-diphenyl indanone compounds are synthesized as follows: substituted triphenylpropionic acid 100 (0.25-0.50 M in sulfuric acid) is stirred at room temperature for 1 hour and then poured into an equal volume of cold water. The aqueous mixture is extracted with an equal volume of ethyl acetate and the organics dried over sodium sulfate. Evaporation gives the desired substituted 3,3-diphenyl indanone compound 102 in about 60-75% yield.

6.2 Synthesis of Substituted 1-Hydroxy-3,3-Diphenyl Indane Compounds

Referring to FIG. 1, substituted 1-hydroxy-3,3-diphenyl indane compounds are synthesized as follows: a solution of substituted 3,3-diphenylindanone 102 (0.25 M in tetrahydrofuran) is added dropwise to 0.25 volume of a 1.0 M solution of lithium aluminum hydride in tetrahydrofuran at 0-5° C. The mixture is warmed to reflux and refluxed for 2.5 h, cooled to 0-5° C. and an equal volume of 1 M HCl added slowly. The mixture is then extracted three times with an equal volume of ethyl acetate. The combined organic extracts are washed with a saturated aqueous solution of sodium bicarbonate and dried over sodium sulfate. Evaporation gives the desired substituted 1-hydroxy-3,3-diphenyl indane compound 104 in about 45-90% yield.

6.3 Synthesis of Substituted 1-N-Oxime-3,3-Diphenyl Indanes

Referring to FIG. 1, substituted 1-N-oxime-3,3-diphenyl indane compounds are synthesized as follows: substituted 3,3-diphenylindanone 102 (1 equivalent) is combined with 5 equivalents of hydroxylamine hydrochloride and 10 equivalents of sodium acetate and dissolved in methanol. The solution is stirred at room temperature for 16 h and then an equal volume of water is added. The mixture is extracted three times with an equal volume of ethyl acetate and the combined organic extracts are dried over sodium sulfate. Evaporation gives the desired substituted 1-N-oxime-3,3-diphenyl indane compound 106 (as a mixture of cis and trans isomers) in about 90-98% yield.

6.4 Synthesis of Substituted 2-Alkyl-3,3-Diphenyl Indanones

Referring to FIG. 1, substituted 2-alkyl-3,3-diphenyl indanone compounds are synthesized as follows: substituted 3,3-diphenyl indanone 102 (1 equivalent) is dissolved in tetrahydrofuran (0.4-1.0 M) and 1.2 equivalents of potassium hydride is added. The mixture is stirred at room temperature until the gas evolution subsides and then the bromoalkane (1.2 equivalents) is added. The mixture is stirred at room temperature and monitored by TLC. The reaction is quenched with water and the mixture extracted with ethyl acetate. The desired substituted 2-alkyl-3,3-diphenyl indanone compound 108 is isolated by silica gel chromatography in about 50-75% yield.

6.5 Synthesis of Substituted 1-Alkoxy-3,3-Diphenyl Indanes

Referring to FIG. 1, substituted 1-alkoxy-3,3-diphenyl indane compounds are synthesized as follows: substituted 1-hydroxy-3,3-diphenylindanone 104 (1 equivalent) is combined with 2 equivalents of sodium hydride in N,N-dimethylformamide and stirred at room temperature until the gas evolution subsides. The haloalkane (2 equivalents) is added and stirred at room temperature for 16-20 hours. An equal volume of water is added and the mixture extracted four times with twice the volume of ethyl acetate. The combined organic extracts are dried over sodium sulfate and the solvent removed in vacuo. The desired substituted 1-alkoxy-3,3-diphenyl indane compound 110 is isolated by vacuum distillation.

6.6 Synthesis of Substituted 3.3-Diohenyl-3H-Indoles

Referring to FIG. 2, substituted 3,3-diphenyl-3H-indole compounds are synthesized as follows: substituted phenyl hydrazine 120 is combined with an equimolar amount of substituted 1,1-diphenyl-2-ketone 122 in phosphoric acid. This mixture is stirred at 100-120° C. until the reaction is complete as determined by TLC. The reaction is cooled to 60-70° C. and diluted with twice the volume of water while stirring. After cooling to room temperature, the mixture is filtered, washed with water, and the crude solid substituted 3,3-diphenyl indole compound 124 is purified by column chromatography or crystallization.

6.7 Synthesis of Substituted 3,3-Diphenyl-3H-Indolines

Referring to FIG. 2, substituted 3,3-diphenyl-3H-indoline compounds are synthesized as follows: substituted 3,3-diphenyl indole compound 124 is reduced with sodium borohydride or sodium cyanoborohydride in a suitable solvent to yield the substituted 3,3-diphenyl-3H-indoline compound 126.

6.8 Synthesis of Substituted N-Substituted-3,3-Diphenyl Indolines

Referring to FIG. 2, substituted N-substituted-3,3-diphenyl indoline compounds are synthesized as follows: substituted 3,3-diphenyl indoline 126 (1 equivalent) is combined with an alkyl halide (1 equivalent) and potassium carbonate (3-4 equivalents) in acetonitrile. The mixture is stirred at reflux until the reaction is complete as determined by TLC. Water and ethyl acetate are added and the mixture is extracted with ethyl acetate. Evaporation of the combined ethyl acetate extracts gives the crude substituted N-substituted-3,3-diphenyl indoline compound 128, which is purified by column chromatography.

6.9 Synthesis of 3,3-Diphenylindanone (Compound 2)

3,3-Diphenylindanone (Compound 2) was synthesized as follows: Triphenylpropionic acid (12 g, 0.04 mol) was stirred in 50 ml concentrated sulfuric acid for 1 hour. The reaction mixture was cooled in an ice bath and diluted with 50 ml water. This mixture was extracted three times with ethyl acetate. The ethyl acetate extracts were combined, dried over sodium sulfate and the solvent removed in vacuo to yield 9.0 g (78% yield) of 3,3-Diphenylindanone (Compound 2) as a white solid having a melting point of 119-123° C.

6.10 Synthesis of 1-Hydroxy-3,3-Diphenylindane (Compound 3)

1-Hydroxy-3,3-Diphenylindane (Compound 3) was synthesized as follows: A solution of 2 g (0.007 mol) 3,3-diphenylindanone (Compound 2) in 20 ml of tetrahydrofuran was added dropwise to a solution of 0.34 g (0.009 mol) LiAlH$_4$ in 10 ml tetrahydrofuran at 0-5° C. The mixture was warmed to reflux and refluxed for 3 hr., cooled to 0-5° C. and 30 ml of 1 M HCl added slowly. The mixture was then extracted three times with 60 ml ethyl acetate. The ethyl acetate extracts were combined, washed with a saturated aqueous solution of sodium bicarbonate and dried over sodium sulfate. Evaporation of the solvent gave 0.9 g (45% yield) of 1-Hydroxy-3,3-Diphenylindane (Compound 3) as white crystals with a melting point of 133-135° C.

6.11 Synthesis of 1-N-Oxime-3,3-Diphenylindane (Compound 4)

1-N-Oxime-3,3-Diphenylindane (Compound 4) was synthesized as follows: 3,3-Diphenylindanone (Compound 2) (2.0 g, 0.007 mol) was combined with 2.4 g (0.035 mol) of hydroxylamine hydrochloride and 5.8 g (0.07 mol) of sodium acetate and dissolved in 30 ml of methanol. The solution was stirred at room temperture for 16 hr and then 100 ml of water was added. The mixture was extracted with 100 ml ethyl acetate and the organic layer dried over sodium sulfate. Evaporation of the solvent gave 1.9 g (90% yield) of 1-N-Oxime-3,3-Diphenylindane (Compound 4) as a white solid having a melting point of 138-141° C.

6.12 Synthesis of Spiro[3,3-diphenyl-2,3-dihydro(1H)indene-1,3'-21-cyanooxirane] (Compound 5) and 2-Cyanomethyl-3,3-diphenylindanone (Compound 9)

Spiro[3,3-diphenyl-2,3-dihydro(1H)indene-1,3'-2'-cyanooxirane] (Compound 5) and 2-cyanomethyl-3,3-diphenylindanone (Compound 9) were synthesized as follows: 3,3-diphenylindanone (Compound 2), 5.0 g (0.0176 mole) and 2.62 g (0.0229 mole) of potassium hydride were stirred at room temperature in 40 mL of tetrahydrofuran. After the gas evolution subsided (approx. 45 min), 1.5 mL (0.0215 mole) of bromoacetonitrile was added. The dark red mixture was stirred for 1 hour and then 50 mL of water was added. The mixture was extracted three times with 75 mL of ethyl acetate. The combined organic extracts were concentrated in vacuo, loaded onto a silica gel column and eluted with 10% ethyl acetate in hexane. Three fractions were collected. After evaporation of the solvent, the first fraction yielded unreacted starting material (3.5 g). The second fraction yielded 0.49 g (9% yield) of spiro[3,3-diphenyl-2,3-dihydro(1H) indene-1,3'-2'-cyanooxirane] (Compound 5) as a white solid. The third fraction yielded 1.05 g (18% yield) of 2-cyanomethyl-3,3-diphenylindanone (Compound 9) as a yellow oil.

6.13 Synthesis of 2-(2'-Propenyl)-1-(2'-propenoxy)-3,3-diphenylindane (Compound 6)

2-(21-Propenyl)-1-(2'-propenoxy)-3,3-diphehylindane (Compound 6) was synthesized as follows: 3,3-diphenylindanone (Compound 2) 2.0 g (0.007 mole) and 0.28 g (0.0084 mole) sodium hydride were stirred at room temperature in 40 mL of dimethylformamide for 1 hour. The reaction mixture was then added drop-wise to 0.64 mL (0.0078 mole) of allyl bromide at −50° C. The mixture was then warmed to reflux and refluxed for 1 hour. After cooling to room temperature, 50 mL of water was added. The mixture was extracted with ethyl acetate, dried over sodium sulfate and concentrated in vacuo. 2-(2'-propenyl)-1-(2'-propenoxy)-3,3-diphenylindane (Compound 6) was isolated in 30% yield as the first fraction from a silica gel column using 10% dichloromethane in hexane as eluate.

6.14 Synthesis of 1-Acetoxy-3,3-diphenylindane (Compound 7)

1-Acetoxy-3,3-diphenylindane (Compound 7) was synthesized as follows: 1-Hydroxy-3,3-diphenylindane (Compound 3) (0.06 g, 0.0021 mol) was combined with 0.3 mL (0.0022 mol) triethylamine in 10 mL of dichloromethane. The mixture was warmed to reflux with stirring to dissolve all of the starting material. The heat was removed and 0.16 mL (0.0022 mol) of acetyl chloride was added to the warm solution. The mixture was returned to reflux and stirred at reflux for 1 h. After cooling to room temperature, the reaction was quenched by adding 5 mL of water. The reaction mixture was extracted with dichloromethane and the organic layer dried over sodium sulfate. Evaporation of the solvent gave 0.008 g (11% yield) of 1-acetoxy-3,3-diphenylindanone (Compound 7) as an off-white solid with a melting point of 90° C.

6.15 Synthesis of 6-Chloro-3,3-di(4-chlorophenyl)indanone (Compound 8)

6-Chloro-3,3-di(4-chlorophenyl)indanone (Compound 8) was synthesized as follows: 3,3,3-Tris(4-chlorophenyl) propionic acid (1.5 g, 0.004 mol) was stirred in 10 mL of concentrated sulfuric acid at room temperature for 1.5 h. The reaction mixture was then poured into 10 mL of ice water and the mixture extracted with dichloromethane. The solvent was evaporated and 0.8 g (54% yield) of 6-Chloro-3,3-di(4-chlorophenyl)indanone (Compound 8) was collected as an off-white solid having a melting point of 134° C.

6.16 Synthesis of 6-Chloro-2-cyanomethyl-3,3-di(4'-chlorophenyl)indanone (Compound 10)

6-Chloro-2-cyanomethyl-3,3-di(4'-chlorophenyl)indanone (Compound 10) was synthesized as follows: 6-Chloro-3,3-di(4'-chlorophenyl)indanone (Compound 8) (1.0 g, 0.0026 mol) was dissolved in 5 mL of tetrahydrofuran and 0.124 g (0.0031 mol) of sodium hydride was added. The reaction mixture was stirred at room temperature for 1.5 h before 0.22 mL (0.0215 mol) of bromoacetonitrile was added. After stirring overnight the reaction was quenched with water and extracted with ethyl acetate. The extracts were combined and the solvent removed in vacuo. The residue was purified on a silica gel column using 5% ethyl acetate in hexane as the eluent. The first fraction from the column was recovered starting material (1.05 g). The second fraction contained undesired side reaction product. The third fraction contained the desired product. After evaporation of the solvent, 0.179 g (16% yield) 6-Chloro-2-cyanomethyl-3,3-di(4'-chlorophenyl)indanone (Compound 10) as a pale yellow solid was obtained.

6.17 Synthesis of 6-Chloro-3,3-di(4'-chlorophenyl)-2-N-oxime-3,3-diphenylindane (Compound 11)

6-Chloro-3,3-di(4'-chlorophenyl)-2-N-oxime-3,3-diphenylindane (Compound 11) was synthesized as follows: 6-Chloro-3,3-di(4'-chlorophenyl)indanone (compound 8) (0.80 g, 0.0021 mol) was combined with 0.72 g (0.0103 mol) of hydroxylamine hydrochloride and 1.69 g (0.0206 mol) of sodium acetate and dissolved in 25 mL of methanol. The solution was stirred at room temperature for 16 h and then water was added. The mixture was extracted with ethyl acetate and theorganic layer was dried over magnesium sulfate. Evaporation of the solvent gave 0.85 g (100% yield) of 6-Chloro-3,3-di(4'-chlorophenyl)-2-N-oxime-3,3-diphenylindane (Compound 11) as a white solid having a melting point of 85° C.

6.18 Synthesis of 2-Acetamide-3,3-diphenylindanone (Compound 12)

2-Acetamide-3,3-diphenylindanone (Compound 12) was synthesized as follows: 2-Cyanomethyl-3,3-diphenylindanone (0.685 g, 0.0021 mol) was combined with 10 mL of concentrated sulfuric acid and 10 mL of glacial acetic acid. The solution was stirred at room temperature for 3 h and then water was added. The mixture was cooled in an ice bath and neutralized to pH 7 with concentrated ammonium hydroxide and then extracted with ethyl acetate. The organic layer was dried over magnesium sulfate. Evaporation of the solvent gave 0.77 g of a light orange solid. This solid was crystallized from a mixture of ethyl acetate and hexane. 2-Acetamide-3,3-diphenylindanone (Compound 12) was obtained as off-white crystals, 0.527 g (73% yield), having a melting point of 169-171° C.

6.19 Synthesis of 2-Cyanomethyl-3,3-diphenylindanol (Compound 13)

2-Cyanomethyl-3,3-diphenylindanol (Compound 13) wassynthesized as follows: 2-cyanomethyl-3,3-diphenylindanone (Compound 2) (0.311 g, 0.001 mol), was dissolved in 5 mL of ethanol at room temperature. Sodium borohydride (0.437 g, 0.011 mol) was added and the mixture was stirred at room temperature for 15 min. The mixture was diluted with ethyl acetate and the pH was adjusted to 2 with 2N hydrochloric acid. The layers were separated and the aqueous layer extracted twice with ethyl acetate. The combined extracts were evaporated in vacuo and the crude product was purified on a silica gel column using 20% ethyl acetate in hexane. The first fraction was unreacted starting material. The second fraction, when the solvent was evaporated, gave 0.16 g (51% yield) of 2-Cyanomethyl-533-diphenylindanol (Compound 13) as a white solid having a melting point of 79-85° C.

6.20 Synthesis of 2-Acetamide-3,3-diphenylindanol (Compound 14)

2-Acetamide-3,3-diphenylindanol (Compound 14) was synthesized as follows: 2-Acetamide-3,3-diphenylindanone (Compound 12) (0.100 g, 0.0003 mol) was dissolved in 2 mL of ethanol and 0.5 mL of methanol at room temperature. Sodium borohydride (0.136 g, 0.0004 mol) was added and the mixture was stirred at room temperature for 3 hours. The mixture was quenched with 2N hydrochloric acid to pH 1. The mixture was extracted with ethyl acetate and the combined extracts dried over magnesium sulfate. Evaporation of the solvent gave an off-white solid which was crystallized from a mixture of ethyl acetate/hexane. 2-Acetamide-3,3-diphenylindanol (Compound 14) was collected by filtration as a white solid (0.026 g, 25% yield) having a melting point of 218-220° C.

6.21 Synthesis of 3,3-Diphenylindanone-2-methyl acetate (Compound 15)

3,3-Diphenylindanone-2-methyl acetate (Compound 15) was synthesized as follows: 3,3-Diphenylindanone (Compound 2) (3.84 g, 0.0135 mol) was dissolved in 30 mL of tetrahydrofuran at room temperature. Potassium hydride (1.85 g, 0.0162 mol) was added and the mixture was stirred at room temperature for 1 hour. Methyl chloroformate (1.25 mL, 0.0162 mol) was added and the mixture was stirred at room temperature for 1 hour. The mixture was quenched with water and extracted with ethyl acetate. The combined extracts were dried over magnesium sulfate. Evaporation of the solvent gave an dark brown solid which was purified on a silica gel column using 5% ethyl acetate in hexane as eluent. The product was collected in the second fraction off the column. Evaporation of the solvent gave a slightly wet, pink solid which was stirred in hexane. 3,3-Diphenylindanone-2-methyl acetate (Compound 15) was collected by filtration as an off-white solid (2.06 g, 45% yield) having a melting point of 140-142° C.

6.22 Synthesis of 3,3-Diphenyl-1-indanyl-2-naphthylmethyl ether (Compound 16)

3,3-Diphenyl-1-indanyl 2-naphthylmethyl ether (compound 16) was synthesized as follows: 1-Hydroxy-3,3-diphenylindane (Compound 3) (0.25 g, 0.87 mmol) was dissolved in 10 mL of dimethylformamide and cooled to 0° C. with stirring. Sodium amide (0.042 g, 1.04 mmol) was added and the reaction stirred for 0.5 h at 0° C. before 0.23 g (1.04 mmol) of 2-bromomethylnaphthalene was added. The reaction mixture was allowed to warm to room temperature and stirred for 15 h. An equal volume of water was added to the mixture and this was extracted twice with 50 mL of ethyl acetate. After drying over magnesium sulfate the solvent was evaporated and the resultant solid was purified on a silica gel column using 2% ethyl acetate in hexane as the eluent. The second fraction collected was the desired product. Evaporation of the solvent gave 0.300 g (81% yield) of 3,3-Diphenyl-1-indanyl 2-naphthylmethyl ether (Compound 16) as an off-white, sticky solid.

6.23 Synthesis of 3,3-Diphenyl-1-indanyl α-(4-methyltoluate) ether (Compound 17)

3,3-Diphenyl-1-indanyl α-(4-methyltoluate) ether (Compound 17) was synthesized as follows: 1-Hydroxy-3,3-diphenylindane (Compound 3) (0.505g, 1.8 mmol) was combined with 0.069 g (2.9 mmol) of sodium amide in 10 mL of dimethylformamide and stirred at room temperature for 1.5 h before 0.667 g (2.9 mmol) of methyl 4-(bromomethyl)benzoate was added. The reaction mixture was stirred for 18 h. The reaction mixture was poured into 50 mL of water and extracted four times with 25 mL of ethyl acetate. The combined extracts were washed with brine, dried over sodium sulfate and the solvent evaporated to yield a yellow oil. The oil was purified by vacuum distillation to give 0.370 g (47% yield) of 3,3-Diphenyl-1-indanyl α-(4-methyltouate) ether (Compound 17) as a yellow solid having a melting point of 50-52° C.

6.24 Synthesis of 3,3-Diphenyl-1-indanyl α-(2-chlorotoluyl) ether (Compound 18)

3,3-Diphenyl-1-indanyl α-(2-chlorotoluyl) ether (Compound 18) was synthesized as follows: 1-Hydroxy-3,3-diphenylindane (Compound 3) (0.503 g, 1.8 mmol) was combined with 0.075 g (3.1 mmol) of sodium amide in 10 mL of dimethylformamide and stirred at room temperature for 1.5 h before 0.40 mL (3.2 mmol) of 2-chlorobenzyl chloride was added. The reaction mixture was stirred for 21 h. The reaction mixture was poured into 50 mL of water and extracted four times with 25 mL of ethyl acetate. The combined extracts were washed with brine, dried over sodium sulfate and the solvent evaporated to yield a yellow oil. The oil was purified by vacuum distillation to give 0.520 g (70% yield) of 3,3-Diphenyl-1-indanyl α-(2-chlorotoluyl) ether (Compound 18) as a solid having a melting point of 27-29° C.

6.25 Synthesis of 3-(3',3'-diphenyl-2'-indanyl-1'-one)protanol (Compound 19)

3-(3',3'-diphenyl-2'-indanyl-1'-one)propanol (Compound 19) was synthesized as follows: 3,3-Diphenylindanone (Compound 2) (2 g, 0.007 mol) was dissolved in 10 mL of tetrahydrofuran, cooled in an ice bath, and 0.97 g (0.0085 mol) of potassium hydride was added. The reaction mixture was stirred at room temperature for 0.5 h before 0.72 mL (0.0077 mol) of 3-bromo-1-propanol was added. After stirring overnight the reaction was quenched with water and extracted with ethyl acetate. The combined extracts were dried over magnesium sulfate and the solvent removed in vacuo. The residue was purified on a silica gel column using 15% ethyl acetate in hexane as the eluent. The first fraction from the column was recovered starting material (1.05 g). The second fraction contained the product. After evaporation of the solvent, 0.84 g (35% yield) of 3-(3',3'-diphenyl-2'-indanyl-1'-one)propanol (Compound 19) as a beige solid having a melting point of 98° C. was obtained.

6.26 Synthesis of 2-(Ethyl-2'-(1,3-dioxolane))-1-hydroxy-3,3-diphenylindene (Compound 20)

2-(Ethyl-2'-(1,3-dioxolane))-1-hydroxy-3,3-diphenylindene (Compound 20) was synthesized as follows: 3,3-Diphenylindanone (Compound 2) (4.0 g, 0.0141 mol) was dissolved in 30 mL of tetrahydrofuran at room temperature. Potassium hydride (2.4 g, 0.0175 mol) was added and the mixture was stirred at room temperature for 0.5 h. 2-(2-Bromoethyl)-1,3-dioxolane (2.0 mL, 0.0170 mol) was added and the mixture was continued stirring overnight at room temperature. The mixture was quenched with water and extracted with ethyl acetate. The combined extracts were purified on a silica gel column using 8% ethyl acetate in hexane followed by 10% ethyl acetate in hexane as eluent. The product was collected in the second fraction off the column. Evaporation of the solvent gave 2-(Ethyl-2'-(1,3-dioxolane))-1-hydroxy-3,3-diphenylindene (Compound 20) as an off-white solid (0.47 g, 9% yield) having a melting point of 124-126° C.

6.27 Other Compounds

Other compounds of the invention can be synthesized by routine modification of the above-described syntheses, or by other methods that are well known in the art. Compound 1 is available from Maybridge Chemical Company (distributor: Ryan Scientific, South Carolina).

7. EXAMPLE

In Vitro Activity

This Example demonstrates the ability of several exemplary compounds of structural formula (I) to inhibit the Gardos channel of erythrocytes (Gardos Channel Assay) and/or mitogen-induced cell proliferation (Mitogenic Assay) in vitro. The assays are generally applicable for demonstrating the in vitro activity of other compounds of structural formula (I).

7.1 Experimental Protocol

The percent inhibition of the Gardos channel (10 μM compound) and the $IC_{50}$ were determined as described in Brugnara et al., 1993, *J. Biol. Chem.* 268(12):8760-8768. The percent inhibition of mitogen-induced cell proliferation (10 μM compound) and the $IC_{50}$ were determined or described in Benzaquen et. al. (1995, *Nature Medicine* 1:534-540) with NIH 3T3 mouse fibroblast cells (ATCC No. CRL 1658). Other cell lines, e.g., cancer cells, endothelial cells and fibroblasts, as well as many others, may be used in the cell proliferation assay. Selection of a particular cell line will depend in part on the desired application, and is well within the capabilities of an ordinarily skilled artisan.

7.2 Results

The results of the experiment are provided in TABLE 1, below. Clotrimazole is reported for purposes of comparison. Most of the compounds tested exhibited significant activity in both assays. All of the compounds tested exhibited significant activity in at least one of the assays.

TABLE 1

Pharmacological Activities of Various Compounds
(% Inhibition measured at 10 μM)

| | Mitogenic Assay | | Gardos Channel Assay | |
|---|---|---|---|---|
| Compound Number | $IC_{50}$ (μM) | Inhibition (%) | $IC_{50}$ (μM) | Inhibition (%) |
| Clotrimazole | 0.626 | 93.0 | 0.046 | 99.3 |
| (1) | 0.700 | 97.0 | 0.419 | 98.0 |
| (2) | 1.300 | 99.0 | 1.006 | 100.0 |
| (3) | 1.100 | 90.0 | 0.819 | 100.0 |
| (4) | 2.600 | 99.0 | 1.350 | 100.0 |
| (5) | — | 29.0 | — | 67.3 |
| (6) | 3.400 | 90.0 | — | 35.0 |
| (7) | 3.400 | 98.0 | 1.152 | 88.0 |
| (8) | 2.000 | 97.0 | 0.176 | 30.0 |
| (9) | — | 45.0 | 0.505 | 100.0 |
| (10) | 3.300 | 98.0 | — | 49.5 |
| (11) | 3.400 | 99.0 | — | 50.0 |
| (12) | — | 31.0 | 0.189 | 99.5 |
| (13) | — | 12.0 | 1.590 | 99.5 |
| (14) | — | 3.0 | 2.961 | 90.5 |
| (15) | 7.500 | 80.0 | 2.901 | 54.8 |
| (16) | — | 75.0 | — | 0 |
| (17) | — | 76.0 | — | 0 |
| (18) | — | 73.0 | — | 0 |
| (19) | 1.500 | 99.0 | 5.952 | 43.7 |
| (20) | — | 81.0 | — | 0 |

8. EXAMPLE

Activity in Cancer Cell Lines

This Example demonstrates the antiproliferative effect of several exemplary compounds of formula (I) against a variety of cancer cell lines. The assays are generally applicable for demonstrating the antiproliferative activity of other compounds of formula (I).

8.1 Growth of Cells

The antiproliferative assays described herein were performed using standard aseptic procedures and universal precautions for the use of tissues. Cells were propagated using RPMI 1640 media (Gibco) containing 2% N 5% fetal calf serum (Biowhittaker) at 37° C., 5% $CO_2$ and 95% humidity. The cells were passaged using Trypsin (Gibco). Prior to addition of test compound, the cells were harvested, the cell number counted and seeded at 10,000 cells/well in 100 μl 5% fetal calf serum (FCS) containing RPMI medium in 964 well plates and incubated overnight at 37° C., 5% $CO_2$ and 95% humidity.

On the day of the treatment, stock solutions of the test compounds (10 mM compound/DMSO) were added in 100 μl FCS containing medium to a final concentration of 10-0.125 μM and the cells were incubated for 2, 3 or 5 days at 37° C., 5% $CO_2$ and 95% humidity.

Following incubation, the cellular protein was determined with the ulforhodamine B (SRB) assay (Skehan P et al., 1990, *J. Natl. Cancer Inst.* 82:1107-1112). Growth inhibition, reported as the concentration of test compound which inhibited 50% of cell proliferation ($IC_{50}$) was determined by curve fitting.

Values for VP-16, a standard anti-cancer agent, are provided for comparison.

Except for MMRU cells, all cancer cell lines tested were obtained from the American Type Culture Collection (ATCC, Rockville, Md.). The ATCC assession numbers were as follows: HeLa (CCL-2); CaSki (CRL-1550); MDA-MB-231 (HTB-26); MCF-7 (HTB-22); A549 (CCL-185); HTB-174 (HTB-174); HEPG2 (HB-8065); DU-145 (HTB-81); SK-MEL-28 (HTB-72); HT-29 (HTB-38); HCT-15 (CCL-225); ACHN (CRL-1611); U-118MG (HTB-15); SK-OV-3 (HTB-77).

MMRU cells (Stender et al., 1993, *J. Dermatology* 20:611-617) were a gift of one of the authors.

8.2 Results

The results of the cell culture assays are presented in TABLES 2 and 3, below.

TABLE 2

SRB ASSAY RESULTS
(5% FCS, 5 Day Incubation)

| | | Test Compound $IC_{50}$ (μM) | | |
|---|---|---|---|---|
| Cancer Type | Cell Line | VP-16 | 8 | 11 |
| Cervical | HeLa | <1.25 | >10 | 5.1 |
| | CaSki | 1.8 | 6.8 | 7 |
| Breast | MDA-MB-23 | <1.25 | >10 | >10 |
| | MCF7 | <1.25 | 5.5 | 4.4 |
| Lung | A549 | <1.25 | 8.9 | 8.8 |
| | HTB174 | <1.25 | >10 | 5.9 |
| Hepatocel | HEPG2 | <1.25 | 6.4 | 5.8 |
| Prostate | DU-145 | <1.25 | >10 | >10 |
| Melanoma | SK-MEL-28 | <1.25 | >10 | 5.5 |
| | MMRU | <1.25 | >10 | 6.2 |
| Colon | HT29 | <1.25 | 8.3 | 6.8 |
| | HCT-15 | 1.3 | >10 | 6.6 |
| Renal | ACHN | <1.25 | >10 | >10 |
| CNS | U118MG | 2.2 | >10 | >10 |
| Ovary | SK-OV-3 | | | >10 |
| Normal human | HUVEC | <1.25 | >10 | 6.4 |
| | GM | 1.4 | >10 | >10 |
| | 3T3 | | >10 | >10 |
| mouse | L929 | <1.25 | >10 | 8.6 |

TABLE 3

SRB RESULTS

| Compound | Conditions % FCS/ days | Test Compound $IC_{50}$ (μM) in Various Cell Lines | | | | | |
|---|---|---|---|---|---|---|---|
| | | A549 | HT29 | MMRU | MCF7 | HEPG2 | U118MG |
| VP-16 | 2%/ 3 days | 2.3 | 20 | <2.5 | <2.5 | | |
| 3 | 5%/ 2 days | >10 | >10 | 5.8 | | | |
| 4 | 2%/ 3 days | 8.5 | <2.5 | 8.2 | <2.5 | | |
| 8 | 5%/ 3 days | >10 | >10 | 3.3 | >10 | 7.8 | >10 |

9. EXAMPLE

Formulations

The following examples provide exemplary, not limiting, formulations for administering the compounds of the invention to mammalian, especially human, patients. Any of the compounds described herein, or pharmaceutical salts or hydrates thereof, may be formulated as provided in the following examples.

9.1 Tablet Formulation

Tablets each containing 60 mg of active ingredient are made up as follows:

| | |
|---|---|
| Active Compound | 60 mg |
| Starch | 45 mg |
| Microcrystalline Cellulose | 45 mg |
| Sodium carboxymethyl starch | 4.5 mg |
| Talc | 1 mg |
| Polyvinylpyrrolidone (10% in water) | 4 mg |
| Magnesium stearate | 0.5 mg |
| | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules are dried at 50°-60° C. and passed through a No. 18 mesh U.S. sieve. The sodium carboxymethyl starch, magnesium stearate and talc, previously passed through a No. 60 mesh U.S. sieve, are then added to the granules, which, after mixing are compressed by a tablet machine to yield tablets each weighing 150 mg.

Tablets can be prepared from the ingredients listed by wet granulation followed by compression.

9.2 Gelatin Capsules

Hard gelatin capsules are prepared using the following ingredients:

| | |
|---|---|
| Active Compound | 250 mg/capsule |
| Starch dried | 200 mg/capsule |
| Magnesium Stearate | 10 mg/capsule |

The above ingredients are mixed and filled into hard gelatin capsules in 460 mg quantities.

9.3 Aerosol Solution

An aerosol solution is prepared containing the following components:

| | |
|---|---|
| Active Compound | 0.25% (w/w) |
| Ethanol | 29.75% (w/w) |
| Propellant 22 (Chlorodifluoromethane) | 77.00% (w/w) |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

9.4 Suppositories

Suppositories each containing 225 mg of active ingredient are made as follows:

| | |
|---|---|
| Active Compound | 225 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

9.5 Suspensions

Suspensions each containing 50 mg of medicament per 5 mL dose are made as follows:

| | |
|---|---|
| Active Compound | 50 mg |
| Sodium carboxymethylcellulose | 50 mg |
| Syrup | 1.25 mL |
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor and some color are diluted with some of the water and added, with stirring. Sufficient water is then added to produce the required volume.

The foregoing written specification is considered to be sufficient to enable one skilled in the art to practice the invention. Various modifications of the above-described modes for carrying out the invention which are obvious to those skilled in the pharmaceutical arts or related fields are intended to be within the scope of the following claims.

All cited references are hereby incorporated in their entireties by reference herein.

What is claimed is:

1. A compound having the structural formula (I):

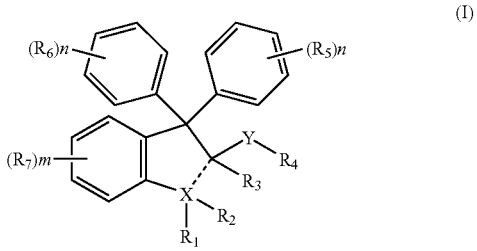

or a pharmaceutically acceptable salt or hydrate thereof wherein:

the bond - - - designates a single or double bond;

m is 0, 1, 2 , 3 or 4;

each n is independently 0, 1, 2, 3, 4 or 5;

X is N;

Y is absent, $(C_1$-$C_6)$ alkyl, $(C_2$-$C_6)$ alkenyl or $(C_2$-$C_6)$ alkynyl;

$R_1$ is absent, —OR, —SR, —O—C(O)R, —S—C(O)R, —O—C(S)R, or —S—C(S)R;

$R_2$ is absent;

$R_3$ is absent or —H;

wherein, when $R_1$ is absent, then $R_3$ is also absent and the bond - - - is a double bond, $R_4$ is —O($C_2$-$C_6$) alkyl, —O($C_2$-$C_6$) alkenyl, —O($C_2$-$C_6$) alkynyl, —S($C_1$-$C_6$) alkyl, —S($C_2$-$C_6$) alkenyl, —S($C_2$-$C_6$) alkynyl, —N(R')$_2$, —CN, —NO$_2$, $(C_3$-$C_8)$ cycloalkyl, 3-8 membered heterocycloalkyl, —C(O)R', —C(S)R', —C(O)OR', —C(S)OR', —C(O)SR', —C(S)SR', —C(O)N(R')$_2$ or —C(S)N(R')$_2$;

each $R_5$, $R_6$ and $R_7$ is independently selected from the group -halogen, —R', —OR', —SR', —N(R')$_2$, —ON (R')$_2$, —SN(R')$_2$, —NO$_2$, —CN, —C(O)R', —C(S)R', —C(O)OR', —C(O)SR', —C(S)OR', —CS(S)R', —C(O)N(R')$_2$, —C(S)N(R')$_2$, —C(O)NR'(OR'), —C(S)NR'(OR'), —C(O)NR'(SR'), —C(S)NR'(SR'), —CH(CN)$_2$, —CH[C(O)R']$_2$, —CH[C(S)R']$_2$, —CH[C(O)OR']$_2$, —CH[C(S)OR']$_2$, —CH[C(O)SR']$_2$ and —CH[C(S)SR']$_2$;

each R is independently selected from the group —H, (C$_1$-C$_6$) alkyl, (C$_2$-C$_6$) alkenyl, (C$_2$-C$_6$) alkynyl, (C$_5$-C$_{20}$) aryl, substituted (C$_5$-C$_{20}$) aryl, (C$_6$-C$_{26}$) alkaryl and substituted (C$_6$-C$_{26}$) alkaryl;

the heterocycloalkyl substituents are each independently selected from the group —CN, —NO$_2$, —N(R')$_2$, —OR', —C(O)N(R')$_2$, —C(S)N(R')$_2$, —C(O)OR', —C(S)OR', —C(O)SR', —C(S)SR' and trihalomethyl;

the aryl and alkaryl substituents are each independently selected from the group -halogen, —C(O)R', —C(S)R', —C(O)OR', —C(S)OR', —C(O)SR', —C(S)SR', —C(O)N(R')$_2$, —C(S)N(R')$_2$ and trihalomethyl; and each R' is independently selected from the group —H, (C$_1$-C$_6$) alkyl, (C$_2$-C$_6$) alkenyl and (C$_2$-C$_6$) alkynyl;

with the proviso that when - - - is a double bond, and R$_1$, R$_3$ and Y are absent, then R$_4$ is other than NH$_2$.

2. A compound having the structural formula (I):

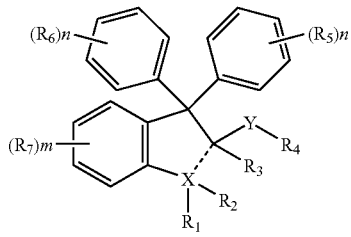

or a pharmaceutically acceptable salt or hydrate thereof, wherein:
the bond - - - designates a single bond;
m is 0, 1, 2, 3 or 4;
each n is independently 0, 1, 2, 3, 4 or 5;
X is N;
Y is absent, (C$_1$-C$_6$) alkyl, (C$_2$-C$_6$) alkenyl or (C$_2$-C$_6$) alkynyl;
R$_1$ is —OR, —SR, —O—C(O)R, —S—C(O)R, —O—C(S)R, or —S—C(S)R;
R$_2$ is absent;
R$_3$ is —H;
R$_4$ is H, OR', —SR', —N(R')$_2$, —CN, —NO$_2$, (C$_3$-C$_8$) cycloalkyl, 3-8 membered heterocycloalkyl, —C(O)R', —C(S)R', —C(O)OR', —C(S)OR', —C(O)SR', —C(S)SR', —C(O)N(R')$_2$ or —C(S)N(R')$_2$;

each R$_5$, R$_6$ and R$_7$ is independently selected from the group -halogen, —R', —OR', —SR', —N(R')$_2$, —ON(R')$_2$, —SN(R')$_2$, —NO$_2$, —CN, —C(O)R', —C(S)R', —C(O)OR', —C(O)SR', —C(S)OR', —CS(S)R', —C(O)N(R')$_2$, —C(S)N(R')$_2$, —C(O)NR'(OR'), —C(S)NR'(OR'), —C(O)NR'(SR'), —C(S)NR'(SR'), —CH(CN)$_2$, —CH[C(O)R']$_2$, —CH[C(S)R']$_2$, —CH[C(O)OR']$_2$, —CH[C(S)OR']$_2$, —CH[C(O)SR']$_2$ and —CH[C(S)SR']$_2$;

each R is independently selected from the group —H, (C$_1$-C$_6$) alkyl, (C$_2$-C$_6$) alkenyl, (C$_2$-C$_6$) alkynyl, (C$_5$-C$_{20}$) aryl, substituted (C$_5$-C$_{20}$) aryl, (C$_6$-C$_{26}$) alkaryl and substituted (C$_6$-C$_{26}$) alkaryl;

the heterocycloalkyl substituents are each independently selected from the group —CN, —NO$_2$, —N(R')$_2$, —OR', —C(O)N(R')$_2$, —C(S)N(R')$_2$, —C(O)OR', —C(S)OR', —C(O)SR', —C(S)SR' and trihalomethyl;

the aryl and alkaryl substituents are each independently selected from the group -halogen, —C(O)R', —C(S)R', —C(O)OR', —C(S)OR', —C(O)SR', —C(S)SR', —C(O)N(R')$_2$, —C(S)N(R')$_2$ and trihalomethyl; and each R' is independently selected from the group —H, (C$_1$-C$_6$) alkyl, (C$_2$-C$_6$) alkenyl and (C$_2$-C$_6$) alkynyl.

3. A compound having the structural formula (I):

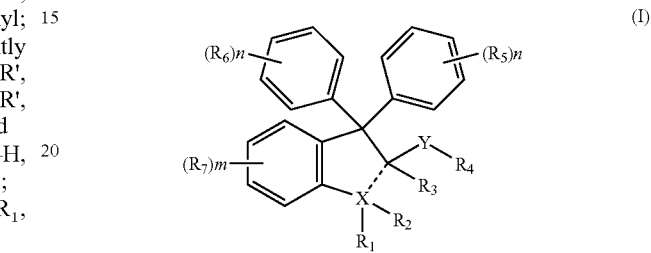

or a pharmaceutically acceptable salt or hydrate thereof wherein:
the bond - - - designates a double bond;
m is 0, 1, 2, 3 or 4;
each n is independently 0, 1, 2, 3, 4 or 5;
X is N;
Y is (C$_2$-C$_6$) alkyl, (C$_2$-C$_6$) alkenyl or (C$_2$-C$_6$) alkynyl;
R$_1$ is absent;
R$_2$ is absent;
R$_3$ is absent;
R$_4$ is H, —O(C$_2$-C$_6$) alkyl, —O(C$_2$-C$_6$) alkenyl, —O(C$_2$-C$_6$) alkynyl, —SR', —N(R')$_2$, —CN, —NO$_2$, (C$_3$-C$_8$) cycloalkyl, 3-8 membered heterocycloalkyl, —C(O)R', —C(S)R', —C(O)OR', —C(S)OR', —C(O)SR', —C(S)SR', —C(O)N(R')$_2$ or —C(S)N(R')$_2$;

each R$_5$, R$_6$ and R$_7$ is independently selected from the group -halogen, —R', —OR', —SR', —N(R')$_2$, —ON(R')$_2$, —SN(R')$_2$, —NO$_2$, —CN, —C(O)R', —C(S)R', —C(O)OR', —C(O)SR', —C(S)OR', —CS(S)R', —C(O)N(R')$_2$, —C(S)N(R')$_2$, —C(O)NR'(OR'), —C(S)NR'(OR'), —C(O)NR'(SR'), —C(S)NR'(SR'), —CH(CN)$_2$, —CH[C(O)R']$_2$, —CH[C(S)R']$_2$, —CH[C(O)OR']$_2$, —CH[C(S)OR']$_2$, —CH[C(O)SR']$_2$ and —CH[C(S)SR']$_2$;

each R is independently selected from the group —H, (C$_1$-C$_6$) alkyl, (C$_2$-C$_6$) alkenyl, (C$_2$-C$_6$) alkynyl, (C$_5$-C$_{20}$) aryl, substituted (C$_5$-C$_{20}$) aryl, (C$_6$-C$_{26}$) alkaryl and substituted (C$_6$-C$_{26}$) alkaryl;

the heterocycloalkyl substituents are each independently selected from the group —CN, —NO$_2$, —N(R')$_2$, —OR', —C(O)N(R')$_2$, —C(S)N(R')$_2$, —C(O)OR', —C(S)OR', —C(O)SR', —C(S)SR' and trihalomethyl;

the aryl and alkaryl substituents are each independently selected from the group -halogen, —C(O)R', —C(S)R', —C(O)OR', —C(S)OR', —C(O)SR', —C(S)SR', —C(O)N(R')$_2$, —C(S)N(R')$_2$ and trihalomethyl; and each R' is independently selected from the group —H, (C$_1$-C$_6$) alkyl, (C$_2$-C$_6$) alkenyl and (C$_2$-C$_6$) alkynyl.

4. A compound having the structural formula (I):

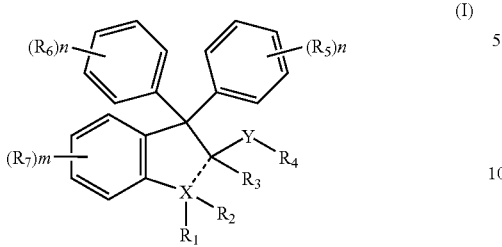

or a pharmaceutically acceptable salt or hydrate thereof, wherein:
- the bond - - - designates a double bond;
- m is 0, 1, 2, 3 or 4;
- each n is independently 0, 1, 2, 3, 4 or 5;
- X is N;
- Y is $(C_1\text{-}C_6)$ alkyl, $(C_2\text{-}C_6)$ alkenyl or $(C_2\text{-}C_6)$ alkynyl;
- $R_1$ is absent;
- $R_2$ is absent;
- $R_3$ is absent;
- $R_4$ is OR', —SR', —N(R')$_2$, —CN, —NO$_2$, $(C_3\text{-}C_8)$ cycloalkyl, 3-8 membered heterocycloalkyl, —C(O)R', —C(S)R', —C(O)OR', —C(S)OR', —C(O)SR', —C(S)SR', —C(O)N(R')$_2$ or —C(S)N(R')$_2$;
- each $R_5$, $R_6$ and $R_7$ is independently selected from the group -halogen, —R', —OR', —SR', —N(R')$_2$, —ON(R')$_2$, —SN(R')$_2$, —NO$_2$, —CN, —C(O)R', —C(S)R', —C(O)OR', —C(O)SR', —C(S)OR', —CS(S)R', —C(O)N(R')$_2$, —C(S)N(R')$_2$, —C(O)NR'(OR'), —C(S)NR'(OR'), —C(O)NR'(SR'), —C(S)NR'(SR'), —CH(CN)$_2$, —CH[C(O)R']$_2$, —CH[C(S)R']$_2$, —CH[C(O)OR']$_2$, —CH[C(S)OR']$_2$, —CH[C(O)SR']$_2$ and —CH[C(S)SR']$_2$;
- each R is independently selected from the group —H, $(C_1\text{-}C_6)$ alkyl, $(C_2\text{-}C_6)$ alkenyl, $(C_2\text{-}C_6)$ alkynyl, $(C_5\text{-}C_{20})$ aryl, substituted $(C_5\text{-}C_{20})$ aryl, $(C_6\text{-}C_{26})$ alkaryl and substituted $(C_6\text{-}C_{26})$ alkaryl;
- the heterocycloalkyl substituents are each independently selected from the group —CN, —NO$_2$, —N(R')$_2$, —OR', —C(O)N(R')$_2$, —C(S)N(R')$_2$, —C(O)OR', —C(S)OR', —C(O)SR', —C(S)SR' and trihalomethyl;
- the aryl and alkaryl substituents are each independently selected from the group -halogen, —C(O)R', —C(S)R', —C(O)OR', —C(S)OR', —C(O)SR', —C(S)SR', —C(O)N(R')$_2$, —C(S)N(R')$_2$ and trihalomethyl; and
- each R' is independently selected from the group —H, $(C_1\text{-}C_6)$ alkyl, $(C_2\text{-}C_6)$ alkenyl and $(C_2\text{-}C_6)$ alkynyl.

5. A pharmaceutical composition comprising an effective amount of one or more compounds as defined in claim 1 and a pharmaceutically acceptable excipient, carrier or diluent.

6. A pharmaceutical composition comprising an effective amount of one or more compounds as defined in claim 2 and a pharmaceutically acceptable excipient, carrier or diluent.

7. A pharmaceutical composition comprising an effective amount of one or more compounds as defined in claim 3 and a pharmaceutically acceptable excipient, carrier or diluent.

8. A pharmaceutical composition comprising an effective amount of one or more compounds as defined in claim 4 and a pharmaceutically acceptable excipient, carrier or diluent.

9. A method of treating a solid tumor selected from the group consisting of cervical cancer, breast cancer, lung cancer, hepatocellular cancer, prostate cancer, melanoma, colon cancer, renal cancer and ovarian cancer, said method comprising the step of administering to a subject in need thereof a therapeutically effective amount of at least one compound having the formula:

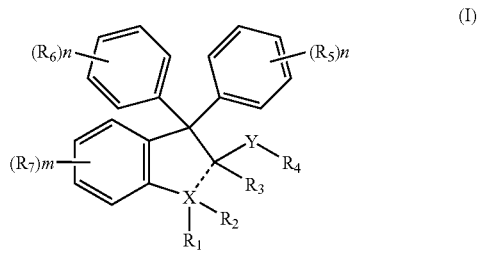

or a pharmaceutically acceptable salt or hydrates thereof, wherein:
- the bond - - - designates a single or double bond;
- m is 0, 1, 2, 3 or 4;
- each n is independently 0, 1, 2, 3, 4 or 5;
- X is N;
- Y is absent, $(C_1\text{-}C_6)$ alkyl, $(C_2\text{-}C_6)$ alkenyl or $(C_2\text{-}C_6)$ alkynyl;
- $R_1$ is absent, —OR, —SR, —O—C(O)R, —S—C(O)R, —O—C(S)R, or —S—C(S)R;
- $R_2$ is absent;
- $R_3$ is absent or —H;
- wherein, when $R_1$ is absent, then $R_3$ is also absent and the bond - - - is a double bond,
- $R_4$ is —H, —OR', —SR', —N(R')$_2$, —CN, —NO$_2$, $(C_3\text{-}C_8)$ cycloalkyl, 3-8 membered heterocycloalkyl, —C(O)R', —C(S)R', —C(O)OR', —C(S)OR', —C(O)SR', —C(S)SR', —C(O)N(R')$_2$ or —C(S)(NR')$_2$;
- each $R_5$, $R_6$ and $R_7$ is independently selected from the group -halogen, —R', —OR', —SR', —N(R')$_2$, —ON(R')$_2$, —SN(R')$_2$, —NO$_2$, —CN, —C(O)R', —C(S)R', —C(O)OR', —C(O)SR', —C(S)OR', —CS(S)R', —C(O)N(R')$_2$, —C(S)N(R')$_2$, —C(O)NR'(OR'), —C(S)NR'(OR'), —C(O)NR'(SR'), —C(S)NR'(SR'), —CH(CN)$_2$, —CH[C(O)R']$_2$, —CH[C(S)R']$_2$, —CH[C(O)OR']$_2$, —CH[C(S)OR']$_2$, —CH[C(O)SR']$_2$ and —CH[C(S)SR']$_2$;
- each R is independently selected from the group —H, $(C_1\text{-}C_6)$ alkyl, $(C_2\text{-}C_6)$ alkenyl, $(C_2\text{-}C_6)$ alkynyl, $(C_5\text{-}C_{20})$ aryl, substituted $(C_5\text{-}C_{20})$ aryl, $(C_6\text{-}C_{26})$ alkaryl and substituted $(C_6\text{-}C_{26})$ alkaryl;
- the heterocycloalkyl substituents are each independently selected from the group —CN, —NO$_2$, —N(R')$_2$, —OR', —C(O)N(R')$_2$, —C(S)N(R')$_2$, —C(O)OR', —C(S)OR', —C(O)SR', —C(S)SR' and trihalomethyl;
- the aryl and alkaryl substituents are each independently selected from the group -halogen, —C(O)R', —C(S)R', —C(O)OR', —C(S)OR', —C(O)SR', —C(S)SR', —C(O)N(R')$_2$, —C(S)N(R')$_2$ and trihalomethyl; and
- each R' is independently selected from the group —H, $(C_1\text{-}C_6)$ alkyl, $(C_2\text{-}C_6)$ alkenyl and $(C_2\text{-}C_6)$ alkynyl.

10. A method of treating a solid tumor selected from the group consisting of cervical cancer, breast cancer, lung cancer, hepatocellular cancer, prostate cancer, melanoma, colon cancer, renal cancer and ovarian cancer, said method comprising the step of administering to a subject in need thereof a therapeutically effective amount of at least one compound having the formula:

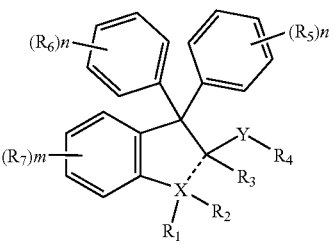

(I)

or a pharmaceutically acceptable salt or hydrates thereof, wherein:

the bond - - - designates a single or double bond;

m is 0 or 1;

each n is independently 0 or 1;

X is N;

Y is absent, $(C_1$-$C_3)$ alkyl, $(C_2$-$C_3)$ alkenyl or $(C_2$-$C_3)$ alkynyl;

$R_1$ is absent, —OR, —O—C(O)R, or —N(R)$_2$;

$R_2$ is absent;

$R_3$ is absent or —H;

wherein when $R_1$ is absent, then $R_3$ is also absent and the bond - - - is a double bond, $R_4$ is —H, —OR, —N(R)$_2$, —CN, —C(O)OR, —C(O)N(R)$_2$ or 5-6 membered dioxoycycloalkyl;

each $R_5$, $R_6$ and $R_7$ is independently selected from the group —R', —F, —Cl or —Br;

each R is independently selected from the group —H, $(C_1$-$C_3)$ alkyl, $(C_2$-$C_3)$ alkenyl, $(C_2$-$C_3)$ alkynyl, $(C_5$-$C_{10})$ aryl, substituted $(C_5$-$C_{10})$ aryl, $(C_6$-$C_{13})$ alkaryl, and substituted $(C_6$-$C_{13})$ alkaryl;

the aryl and alkaryl substituents are each independently selected from the group —F, —Cl, —Br, —CN, —NO$_2$, —N(R')$_2$, —C(O)R', —C(O)OR' and trihalomethyl; and R' is —H, $(C_1$-$C_3)$ alkyl, $(C_2$-$C_3)$ alkenyl or $(C_2$-$C_3)$ alkynyl.

11. The method of claim 10, wherein said compound is

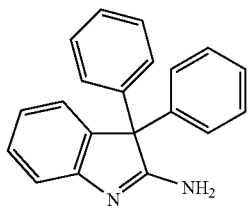

12. A method of treating a solid tumor selected from the group consisting of cervical cancer, breast cancer, lung cancer, hepatocellular cancer, prostate cancer, melanoma, colon cancer, renal cancer and ovarian cancer, said method comprising the step of administering to a subject in need thereof a therapeutically effective amount of the pharmaceutical composition according to any one of claims 5 to 8.

13. A method of treating a solid tumor selected from the group consisting of cervical cancer, breast cancer, lung cancer, hepatocellular cancer, prostate cancer, melanoma, colon cancer, renal cancer and ovarian cancer, said method comprising the step of administering to a subject in need thereof a therapeutically effective amount of the pharmaceutical composition comprising a compound of formula:

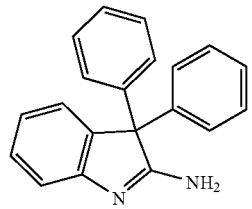

and a pharmaceutically acceptable excipient, carrier or diluent.

14. The method of claim 12, wherein said step of administering is per oral, parenteral or intravenous.

15. The method of claim 13, wherein said step of administering is per oral, parenteral or intravenous.

* * * * *

UNITED STATES PATENT AND TRADEMARK OFFICE
CERTIFICATE OF CORRECTION

| | | |
|---|---|---|
| PATENT NO. | : 7,342,038 B2 | Page 1 of 1 |
| APPLICATION NO. | : 10/858975 | |
| DATED | : March 11, 2008 | |
| INVENTOR(S) | : Carlo Brugnara et al. | |

It is certified that error appears in the above-identified patent and that said Letters Patent is hereby corrected as shown below:

Title Page; item (62):
*On page 1, under "Related U.S. Application Data": Replace* "Division of Ser. No. 10/043,640, filed on Jan. 10, 2002, now Pat. No. 6,800,658." *with* --Division of Ser. No. 10/043,640, filed on Jan. 10, 2002, now Pat. No. 6,800,658, which is a continuation of Ser. No. 09/554,849, filed on Sep. 22, 2000, abandoned, which is a 371 of PCT/US98/24819 filed on Nov. 20, 1998, which is a continuation-in-part and claims the benefit of Ser. No. 08/975,391 filed on Nov. 20, 1997, abandoned.--

*From column 1, line 8 through column 1, line 17: Replace* "This application is a divisional (and claims the benefit of priority under 35 USC 120) of U.S. application Ser. No. 10/043,640, filed Jan. 10, 2002 now U.S. Patent No. 6,800,658, which claims benefit of U.S. application Ser. No. 09/554,849, filed Sep. 22, 2000, now abandoned, which claims benefit of Ser. No. 09/535,077, filed Mar. 23, 2000, now abandoned, which claims benefit of Ser. No. 09/472,859, filed Dec. 27, 1999, which claims priority under 371 of PCT/US98/24819, filed Nov. 20, 1998, which claims benefit of Ser. No. 08/975,391, filed Nov. 20, 1997, now abandoned." *with* --This application is a divisional and claims the benefit of priority from Ser. No. 10/043,640, filed on Jan. 10, 2002, now Pat. No. 6,800,658, which is a continuation and claims the benefit of priority from Ser. No. 09/554,849, filed on Sep. 22, 2000, abandoned, which is a 371 and claims the benefit of priority from PCT/US98/24819, filed on Nov. 20, 1998, which is a continuation-in-part and claims the benefit of priority from Ser. No. 08/975,391, filed on Nov. 20, 1997, abandoned.--

Signed and Sealed this

Twelfth Day of August, 2008

JON W. DUDAS
*Director of the United States Patent and Trademark Office*